(12) United States Patent
Adams

(10) Patent No.: US 7,276,073 B2
(45) Date of Patent: Oct. 2, 2007

(54) STRAIGHTENING TOOLS HAVING GUIDE TEMPLATES FOR ANGLED TISSUE CUTTING INSTRUMENTS AND METHODS OF USING THE SAME

(75) Inventor: Kenneth M. Adams, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 642 days.

(21) Appl. No.: 10/429,723

(22) Filed: May 6, 2003

(65) Prior Publication Data

US 2004/0225308 A1 Nov. 11, 2004

(51) Int. Cl.
*A61B 17/32* (2006.01)
*B21D 5/04* (2006.01)

(52) U.S. Cl. .......................... 606/167; 72/310; 72/319; 140/106; 140/147

(58) Field of Classification Search ................. 72/310, 72/319, 367–369, 31.05, 31.09, 31.1, 31.11, 72/31.112, 458–468, 388, 475, 479, 457; 140/106, 147; 606/167
See application file for complete search history.

(56) References Cited

U.S. PATENT DOCUMENTS

| | | | |
|---|---|---|---|
| 177,490 A | | 5/1876 | Fones et al. |
| 3,154,115 A | * | 10/1964 | Busl ............................ 140/147 |
| 3,236,089 A | * | 2/1966 | Lohouse Jr. ................. 72/458 |
| 3,722,256 A | * | 3/1973 | Iascone ....................... 72/470 |
| 4,052,881 A | | 10/1977 | Mount |
| 4,445,509 A | | 5/1984 | Auth |
| 4,466,429 A | | 8/1984 | Loscher et al. |
| 4,646,738 A | | 3/1987 | Trott |
| 4,926,672 A | * | 5/1990 | Swanson ..................... 72/458 |
| 5,152,744 A | | 10/1992 | Krause et al. |
| 5,286,253 A | | 2/1994 | Fucci |
| 5,322,505 A | | 6/1994 | Krause et al. |
| 5,411,514 A | | 5/1995 | Fucci et al. |

(Continued)

OTHER PUBLICATIONS

Website product information brochure, Medtronic Xomed Product Spotlight, RAD® Curved Blades, Dec. 31, 2003. 3 pgs.

(Continued)

*Primary Examiner*—Glenn K. Dawson
*Assistant Examiner*—Amanda Adams

(57) ABSTRACT

A straightening tool for straightening an elongate angled member of an angled tissue cutting instrument in which the elongate angled member has a proximal length portion and an initial bend connecting the proximal length portion to a distal length portion extending from the bend to a distal end. The straightening tool comprises a positioning block attached to a handle, an unbending channel in the positioning block configured to effect straightening of the elongate angled member and a guide template corresponding to the unbending channel. The guide template comprises a guide slot having a longitudinal profile corresponding to the longitudinal profile of a forward aspect of the elongate angled member extending from the distal end proximally of the bend. A method of straightening an elongate angled member of an angled tissue cutting instrument involves matching the longitudinal profile of a forward aspect of the elongate angled member to a guide template of a straightening tool, inserting the forward aspect into an unbending channel of the straightening tool corresponding to the guide template, straightening the elongate angled member using the unbending channel and withdrawing the straightened elongate member from the unbending channel.

17 Claims, 7 Drawing Sheets

U.S. PATENT DOCUMENTS

| | | |
|---|---|---|
| 5,437,630 A | 8/1995 | Daniel et al. |
| 5,529,580 A | 6/1996 | Kusunoki et al. |
| 5,601,506 A | 2/1997 | Long et al. |
| 5,601,586 A * | 2/1997 | Fucci et al. .................. 606/180 |
| 5,620,415 A | 4/1997 | Lucey et al. |
| 5,620,447 A | 4/1997 | Smith et al. |
| 5,782,795 A | 7/1998 | Bays |
| 5,819,571 A | 10/1998 | Johnson |
| 5,916,231 A | 6/1999 | Bays |
| 5,922,003 A | 7/1999 | Anctil et al. |
| 5,957,881 A | 9/1999 | Peters et al. |
| 6,010,477 A | 1/2000 | Bays |
| 6,183,433 B1 | 2/2001 | Bays |
| 6,293,957 B1 | 9/2001 | Peters et al. |
| 6,312,438 B1 | 11/2001 | Adams |
| 7,131,975 B2 * | 11/2006 | Adams ....................... 606/101 |
| 2002/0193811 A1 | 12/2002 | Chan |

OTHER PUBLICATIONS

Website product information brochure, Medtronic Xomed Surgical Techniques. Powered Adenoidectomy Using the RADenoid® Blade, Dec. 31, 2003. 3 pgs.

* cited by examiner

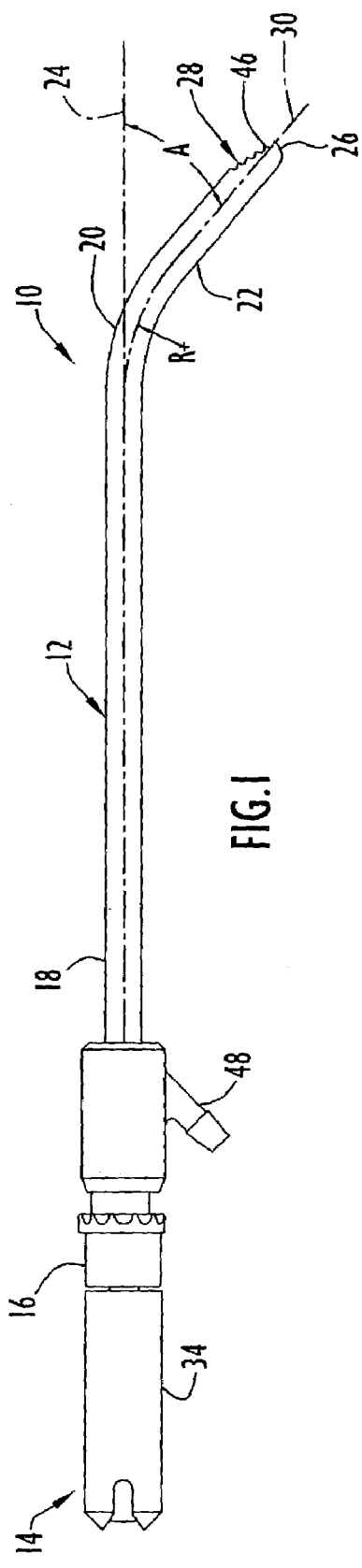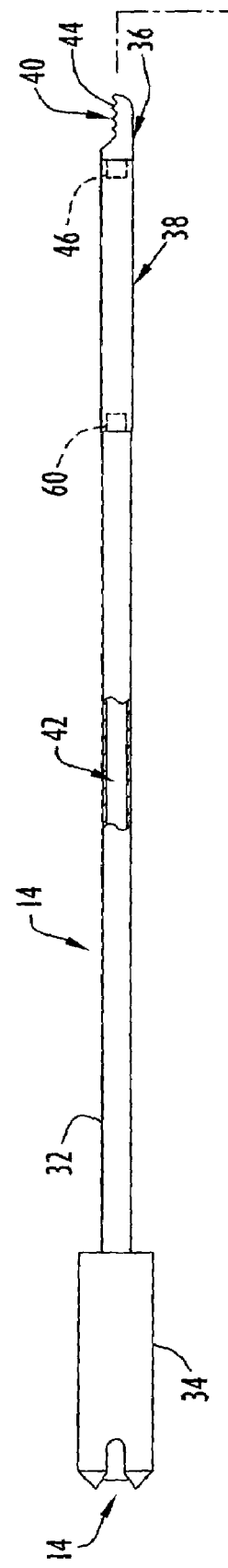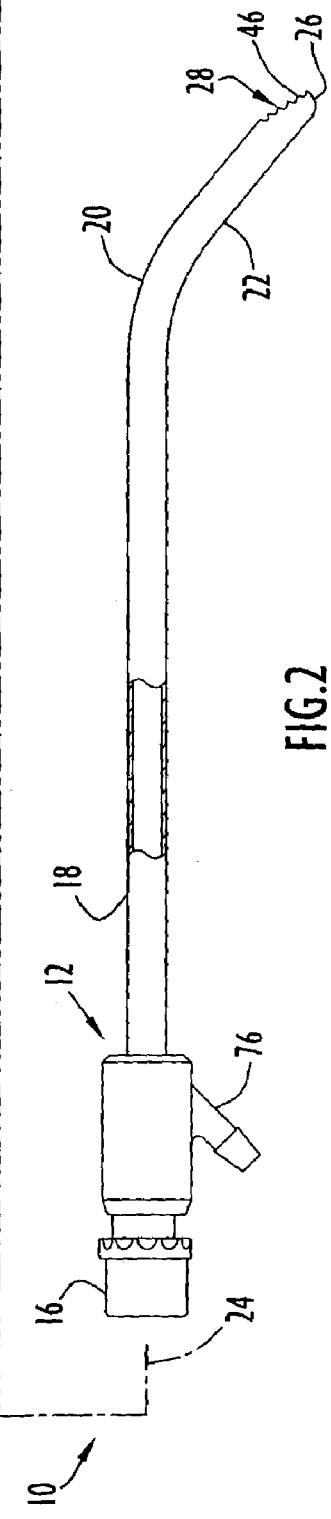

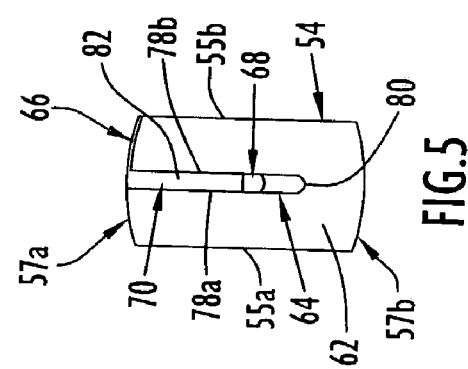
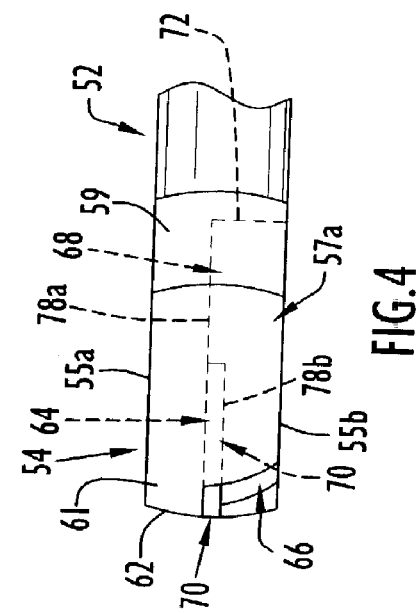
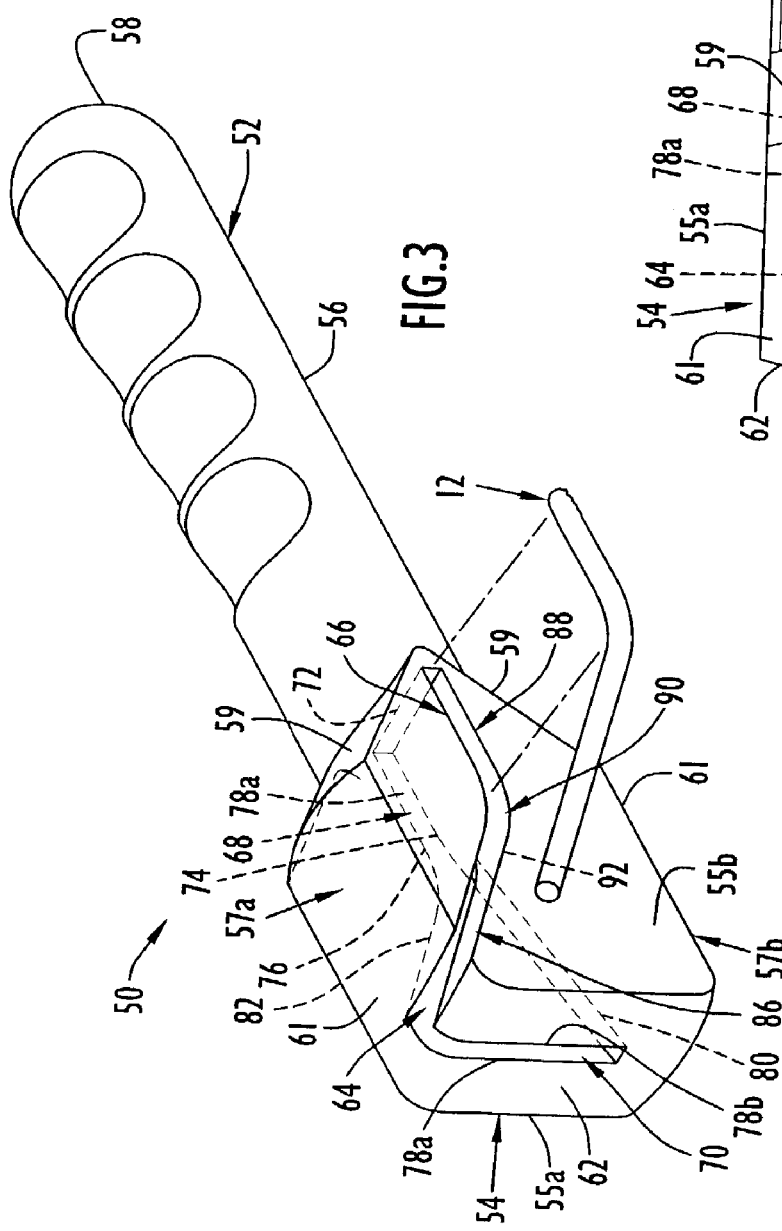

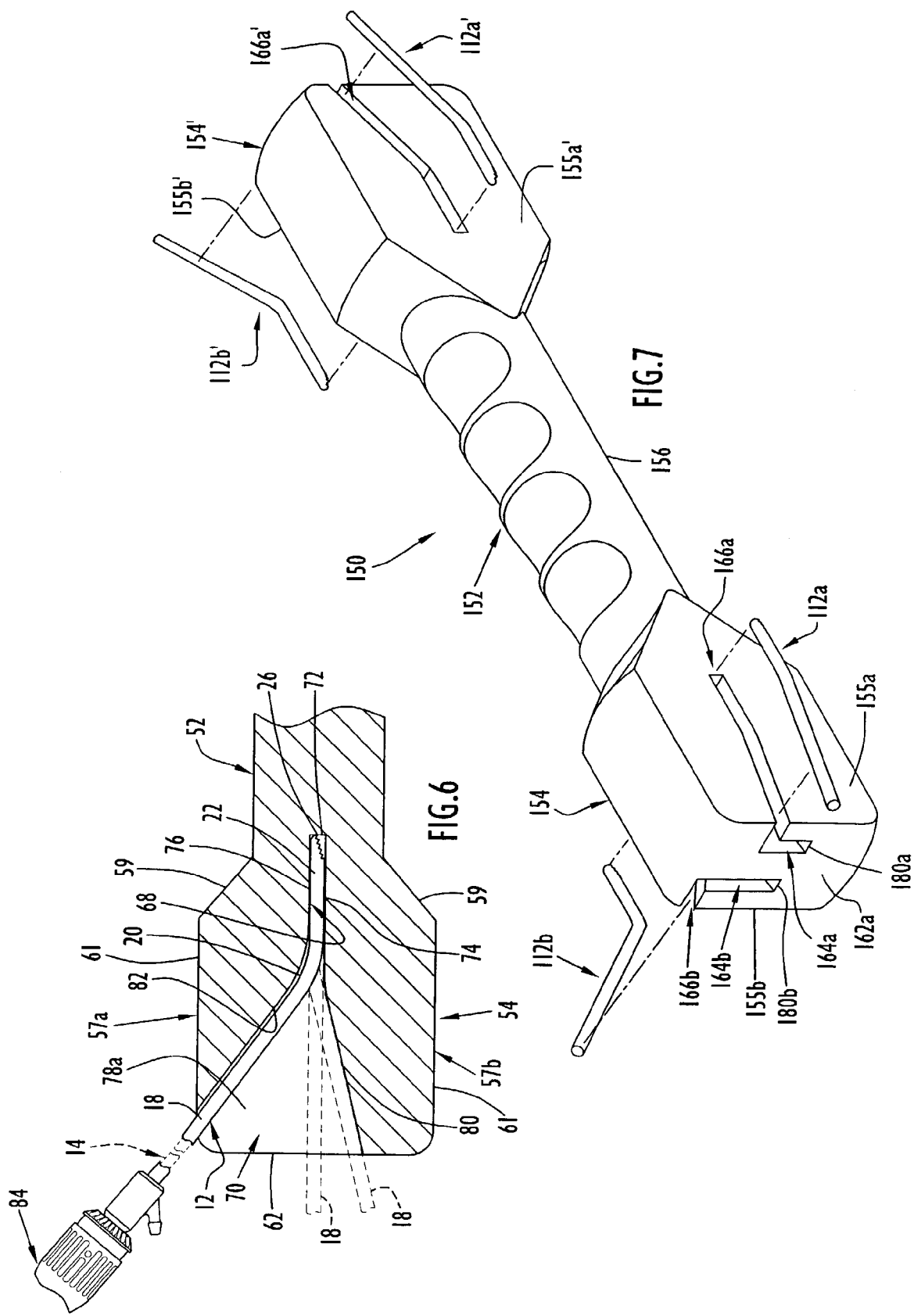

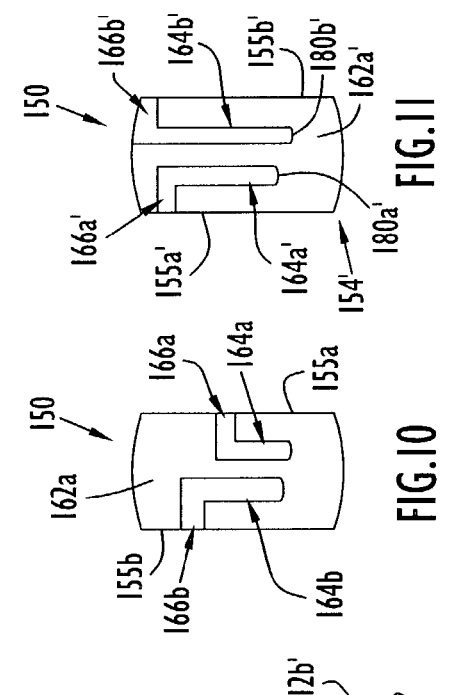
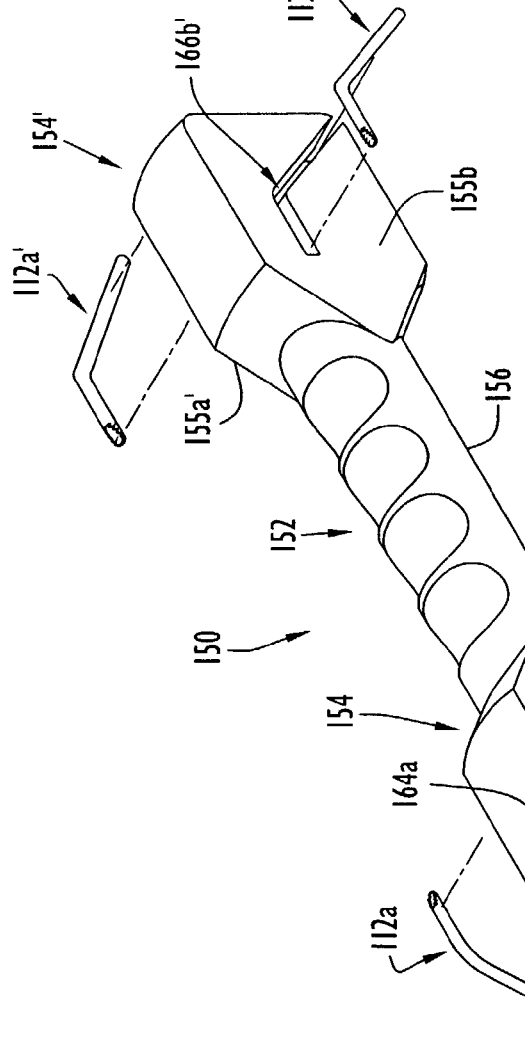
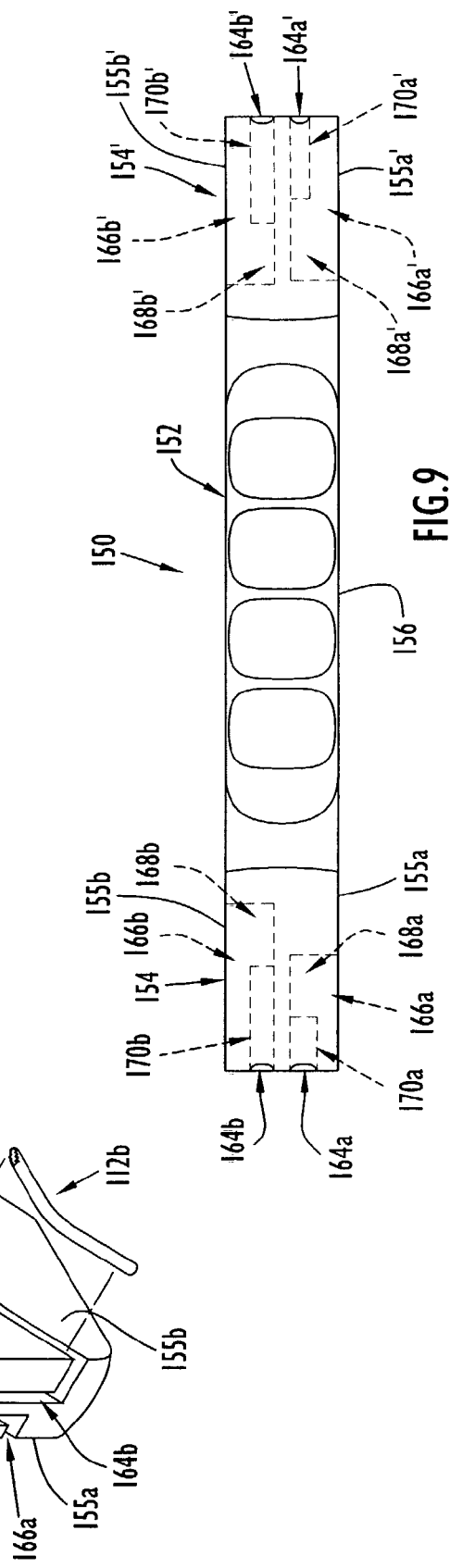

STRAIGHTENING TOOLS HAVING GUIDE TEMPLATES FOR ANGLED TISSUE CUTTING INSTRUMENTS AND METHODS OF USING THE SAME

CROSS-REFERENCE TO RELATED PATENT APPLICATION

This application is related to prior U.S. patent application Ser. No. 10/244,062 filed Sep. 16, 2002, the entire disclosure of which is incorporated herein by reference.

BACKGROUND OF THE INVENTION

1. Field of the Invention

The present invention relates generally to angled tissue cutting instruments and, more particularly, to apparatus and methods for straightening the bends of angled tissue cutting instruments.

2. Brief Discussion of the Related Art

Tissue cutting instruments comprising an elongate outer tubular member and an elongate inner member rotatably disposed in the outer tubular member to cut anatomical tissue have become well accepted for use in various surgical procedures. Typically, the inner member has a distal end with a cutting edge and the outer member has an opening through which the cutting edge is exposed to access anatomical tissue to be cut by the cutting edge when the inner member is rotated within the outer member. The cutting edge may have various configurations in accordance with the type of tissue and/or the type of cutting action to be accomplished. In some instances, the distal end of the outer member has a cutting edge cooperable with the cutting edge of the inner member to cut the anatomical tissue as the inner member is rotated. The outer and inner members ordinarily have proximal ends adapted for coupling with a powered surgical handpiece used to rotate the inner member relative to and within the outer member. Many tissue cutting instruments provide for aspiration of anatomical debris through the tissue cutting instrument and/or irrigation at the operative site via an irrigating or flushing fluid supplied along the tissue cutting instrument.

In tissue cutting instruments of the foregoing type, the outer members may be longitudinally or axially straight or may be longitudinally or axially bent, angled or curved depending on the surgical procedure being performed. Where the outer member is longitudinally or axially bent, angled or curved, the inner member is normally provided with a flexible region adjacent or within the bend, angle or curve in the outer member whereby the inner member assumes the longitudinally or axially bent, angled or curved configuration of the outer member while still being rotatable within the outer member. Angled tissue cutting instruments of the latter type are represented by U.S. Pat. No. 177,490 to Fones, U.S. Pat. No. 4,445,509 to Auth, U.S. Pat. No. 4,466,429 to Loscher, U.S. Pat. No. 4,646,738 to Trott, U.S. Pat. No. 5,152,744 and U.S. Pat. No. 5,322,505 to Krause et al, U.S. Pat. No. 5,286,253, U.S. Pat. No. 5,411,514 and U.S. Pat. No. 5,601,586 to Fucci et al, U.S. Pat. No. 5,437,630 to Daniel et al, U.S. Pat. No. 5,529,580 to Kusumoki et al, U.S. Pat. No. 5,620,415 to Lucy et al, U.S. Pat. No. 5,620,447 to Smith et al and U.S. Pat. No. 5,922,003 to Anctil et al.

In most angled tissue cutting instruments, the bend, curve or angle is pre-formed in the outer member as part of the manufacturing or fabrication process and is essentially rigid or fixed. However, U.S. Pat. No. 5,601,586 and No. 5,411,514 to Fucci et al are representative of variable angle tissue cutting instruments in which a longitudinally straight outer member has a spiral relief cut forming a non-rigid bendable section along which the outer member may be bent axially by a user, and the inner member is flexible to follow the bent configuration of the outer member. Accordingly, the Fucci et al patents are representative of angled tissue cutting instruments in which the bend is pre-formed in the outer member subsequent to the manufacturing process and is essentially non-rigid or variable. The Fucci et al patents also disclose bending tools permitting a user to bend the longitudinally straight outer member axially along the non-rigid bendable section to assume various predetermined angles.

The bending tools disclosed in the Fucci et al patents operate by bending a longitudinally straight outer tube into contact with an angled limit surface disposed at a greater angle than the bend angle to be created in the outer tube and then allowing the outer tube to spring back in a direction away from the limit surface to obtain the bend angle. The angles of the limit surfaces specifically provide for a spring back to create a significant positive bend angle in the outer tube, and the bending tools are not designed with limit surfaces capable of providing a spring back for unbending or straightening an already bent or angled outer tube to obtain a longitudinally straightened outer tube.

Angled tissue cutting instruments in which the outer members are pre-formed with an essentially fixed bend, angle or curve may advantageously be precision manufactured with the bend, angle or curve formed with exactitude to extend in a pre-selected direction at a specified location and angle with a predetermined radius of curvature. Accordingly, the outer member can be manufactured with a preformed angle, bend or curve that is optimal for the surgical procedure being performed. As an example, the outer member can have a pre-formed bend, curve or angle that is optimal for use of the instrument as an adenoid blade. In many surgical procedures facilitated by an angled tissue cutting instrument, it is preferable that the outer member be pre-formed with the most desirable or advantageous bend, curve or angle for the particular surgical procedure to ensure that the most optimal outer member configuration is used for the particular surgical procedure.

In some surgical procedures, it is desirable to utilize angled tissue cutting instruments to remove anatomical tissue and to thereafter utilize longitudinally or axially straight tissue cutting instruments for further removal of anatomical tissue. In a combined tonsillectomy and adenoidectomy (T&A) procedure, for instance, an adenoidectomy is performed prior to a tonsillectomy to remove all or part of an adenoid using an angled tissue cutting instrument as represented by the adenoid blade disclosed in the aforementioned Anctil et al patent and by the RADenoid® Blade of Medtronic Xomed Surgical Products, Inc. The tonsillectomy is thereafter performed, typically utilizing the same angled tissue cutting instrument or another different tissue cutting instrument in which the outer member is longitudinally or axially straight. Performing the tonsillectomy using the angled tissue cutting instrument that was used for the adenoidectomy, i.e. the adenoid blade, is disadvantageous since longitudinally or axially straight tissue cutting instruments provide better access to the tonsils. Using another different tissue cutting instrument having a longitudinally or axially straight outer member for the tonsillectomy is also disadvantageous for the increased cost associated with an additional instrument and/or the additional surgical time associated with preparing the additional instrument for use. The added steps involved in preparing an additional instrument for use during surgery may include removing the instrument from its package, assembling the inner member of the instrument within the outer member, coupling the inner member and the outer member to the surgical handpiece, and/or removing the angled tissue cutting instrument from the surgical handpiece so that the same handpiece can be coupled with the inner and outer members of the additional instrument. Furthermore, the need to inventory and supply both angled and straight tissue cutting instruments for a surgical procedure imposes a difficult burden on hospitals and other surgical sites.

In various sinus procedures, it is also common for surgeons to initially utilize an angled tissue cutting instrument to remove anatomical tissue and to thereafter utilize a straight tissue cutting instrument to further remove anatomical tissue. The Rad® 40 Curved Blade and the Rad 60 X-TREME™ Curved Blade of Medtronic Xomed Surgical Products are representative of angled tissue cutting instruments which allow access into the frontal recess and maxillary sinus and are popular for use in sinus surgery, particularly superior ethmoid and frontal recess surgery, removal of maxillary polyps, uncinectomy and antrostomy. During sinus surgery where tissue removal is initially effected using an angled tissue cutting instrument, the surgeon will sometimes switch to a longitudinally straight tissue cutting instrument where needed to afford better access for further tissue removal. As discussed above, the need to switch between two different instruments during a surgical procedure presents numerous drawbacks.

Sometimes angled tissue cutting instruments having blades with a particular distal end cutting configuration are available to surgeons without there being available straight tissue cutting instruments having the particular distal end cutting configuration. There arises an unsatisfied need where a surgeon desires to use the particular distal end cutting configuration of an available angled tissue cutting instrument but as a longitudinally straight tissue cutting instrument. Accordingly, an angled tissue cutting instrument may have to be used in a surgical procedure in which use of a counterpart straight tissue cutting instrument would be more preferable.

Where an angled tissue cutting instrument is to be used in a surgical procedure alone or prior to using a longitudinally straight tissue cutting instrument, the need to bend an initially straight outer tube to obtain the angled tissue cutting instrument as required by the Fucci et al patents is undesirable for the additional time and procedural steps added to the surgical procedure. An angled tissue cutting instrument having a bent outer tube obtained using the bending tools of the Fucci et al patents cannot thereafter be reliably straightened for use as a longitudinally straight tissue cutting instrument since the bending tools are incapable of reversely bending a previously bent outer tube with any degree of precision or control to obtain a longitudinally straight outer tube.

It is seen from the above that a need exists for apparatus and methods to effect controlled unbending or straightening of an angled, bent or curved member of an angled tissue cutting instrument to obtain a longitudinally or axially straight tissue cutting instrument therefrom. Apparatus and methods are needed which are capable of accomplishing unbending or straightening of an angled tissue cutting instrument prior to or during a surgical procedure in a brief amount of time using a minimal number of simple procedural steps. In particular, apparatus and methods are needed for unbending or straightening an angled tissue cutting instrument for use as a longitudinally straight tissue cutting instrument during a surgical procedure to ensure that the instrument has both the optimal distal end cutting configuration and the optimal longitudinal profile for the surgical procedure and/or to eliminate the need for surgeons to switch between different instruments during the surgical procedure. There is also a need to reduce the number of different instruments required to be made available for and/or used during a surgical procedure to reduce surgical costs and the burden on hospitals and other surgical sites associated with maintaining and supplying many different instruments. Especially in the areas of T&A procedures and sinus procedures, the need exists for allowing a pre-formed angled tissue cutting instrument to be used in a surgical procedure to remove anatomical tissue and to be thereafter straightened or unbent for further use in the surgical procedure to remove anatomical tissue as a longitudinally straight tissue cutting instrument. There is also a need to permit an available angled tissue cutting instrument having a particular distal end cutting configuration desirable for use in a surgical procedure to be straightened or unbent prior to the surgical procedure to assume a straight longitudinal profile that is more preferable for the surgical procedure than an angled longitudinal profile. There is a further need for an unbending or straightening tool having a contact surface against which an angled member of an angled tissue cutting instrument is reversely bent and then allowed to spring back in a direction away from the contact surface to obtain a longitudinally straight member. An unbending or straightening tool for angled tissue cutting instruments is needed having a contact surface at the proper angle to controllably unbend the angled members of the angled tissue cutting instruments to obtain longitudinally straight members after accounting for springback of the members. An additional need prevails for an unbending or straightening tool having a guide template allowing a particular angled member to be matched with the guide template for unbending using an unbending channel of the tool corresponding to the guide template. A still further need exists for an unbending tool having a plurality of unbending channels for angled members of different longitudinal profiles, respectively, and a guide template for each unbending channel to facilitate matching the different angled members with the appropriate unbending channels.

SUMMARY OF THE INVENTION

The present invention is generally characterized in a straightening tool for straightening an elongate angled member of an angled tissue cutting instrument in which the elongate angled member has a proximal length portion and an initial bend connecting the proximal length portion to a distal length portion extending from the bend to a distal end. The straightening tool comprises a positioning block attached to a handle, an unbending channel in the positioning block and a guide template corresponding to the unbending channel. The unbending channel is configured to effect straightening of the elongate angled member. The guide template comprises a guide slot disposed along an external wall of the positioning block and having a longitudinal profile corresponding to the longitudinal profile of a forward aspect of the elongate angled member. In one embodiment, the guide template includes a first length section corresponding to part of the proximal length portion of the elongate angled member extending from the initial bend, an angled length section corresponding to the initial bend of the elongate angled member and a second length section corresponding to the distal length portion of the elongate angled member. Where the proximal and distal length portions of the elongate angled member are straight, the first and second length sections of the guide template are correspondingly straight with the angled length segment being bent, curved or angled to correspond to the initial bend of the elongate angled member. The longitudinal profile of the elongate angled member to which the longitudinal profile of the guide template corresponds includes the bend, curve or angle, the working length and the outer diameter of the angled member along the forward aspect. The guide slot is thusly configured and sized to receive the longitudinal profile of the forward aspect of the elongate angled member with a complementary or close fit, and the guide slot may be in communication with the unbending channel to allow the forward aspect to be moved along the guide slot and into the unbending channel. The guide template relates or corresponds to the unbending channel and, by matching the angled member to the guide template, the angled member is matched to the most optimal unbending channel to effect straightening of the angled member. The unbending channel may have an upper surface conforming to the longitudinal profile of the angled member along its forward aspect and to the upper surface of the guide template. The unbending channel comprises a confinement passage for confining the distal length portion of the elongate angled member against movement in a direction radial or transverse to a longitudinal axis of the distal length portion while permitting pivotal movement of the proximal length portion in a direction opposite the initial bend and relative to the distal length portion confined in the confinement passage. The unbending channel may have a contact surface against which the proximal length portion is reversely bent, and the contact surface is angled from the confinement passage at an angle to obtain straightening of the angled member after spring back in the direction of the initial bend. The straightening tool may comprise a plurality of unbending channels configured to effect straightening of a plurality of elongate angled members having different longitudinal profiles along their forward aspects and a plurality of corresponding guide templates matching the longitudinal profiles of the forward aspects of the different elongate angled members, respectively. The straightening tool may comprise a single positioning block having a plurality of unbending channels and guide templates corresponding thereto. The straightening tool may comprise a plurality of positioning blocks, each having one or more unbending channels and corresponding guide templates.

The present invention is also generally characterized in a method of straightening an elongate angled member of an angled tissue cutting instrument in which the elongate angled member has a proximal length portion and an initial bend connecting the proximal length portion to a distal length portion extending from the bend to a distal end. The method involves the steps of matching the longitudinal profile of a forward aspect of the elongate angled member to a guide template of a straightening tool, inserting the forward aspect into an unbending channel of the straightening tool corresponding to the guide template that was matched to the elongate angled member, confining the distal length portion in a confinement passage of the unbending channel to confine the distal length portion against movement in a direction radial or transverse to a longitudinal axis of the distal length portion, applying force to the elongate angled member to forcefully pivot the proximal length portion in a direction opposite the initial bend and relative to the distal length portion confined in the confinement passage, releasing the force applied to the elongate member to allow the proximal length portion to spring back in the direction of the initial bend to obtain a straight elongate member, and withdrawing the straight elongate member from the unbending channel. The longitudinal profile of the forward aspect that is matched to the guide template may include the distal length portion, the initial bend and part of the proximal length portion extending from the initial bend. The longitudinal profile of the forward aspect may be visually matched to the guide template via a side-by-side comparison and/or may be inserted in the guide template with a complementary fit. Insertion of the forward aspect into the unbending channel may be accomplished by moving the forward aspect within and along the guide template into the unbending channel in communication with the guide template. The proximal length portion may be forcefully pivoted manually, and the proximal length portion may be pivoted into contact with a contact surface of the straightening tool disposed at an angle to the confinement passage such that a reverse positive bend is imparted to the elongate member opposite the initial bend prior to the elongate member springing back in the direction of the initial bend. The step of matching may involve matching the longitudinal profile of the forward aspect of the elongate angled member to one of a plurality of different guide templates of the straightening tool corresponding to a plurality of different unbending channels of the straightening tool, respectively, and the step of inserting may include inserting the forward aspect into the unbending channel which corresponds to the matching guide template.

BRIEF DESCRIPTION OF THE DRAWINGS

FIG. 1 is a side view of an angled tissue cutting instrument or blade.

FIG. 2 is an exploded side view, partly in section, of the angled tissue cutting instrument.

FIG. 3 is a broken perspective view depicting the forward aspect of an elongate angled member of the angled tissue cutting instrument of FIG. 1 matched to a guide template of a straightening or unbending tool.

FIG. 4 is a broken top view of the straightening tool.

FIG. 5 is an end view of the straightening tool.

FIG. 6 is a broken longitudinal sectional view of the straightening tool illustrating straightening of the angled member using an unbending channel of the straightening tool corresponding to the matching guide template.

FIG. 7 is a broken perspective view illustrating an alternative straightening tool according to the present invention having a plurality of different guide templates corresponding to a plurality of different unbending channels, respectively, for a plurality of different elongate angled members, respectively, of angled tissue cutting instruments.

FIG. 8 is a broken perspective view showing the alternative straightening tool and the plurality of different elongate angled members rotated 180°.

FIG. 9 is a top view of the alternative straightening tool.

FIG. 10 is an end view of the alternative straightening tool.

FIG. 11 is an opposite end view of the alternative straightening tool.

DESCRIPTION OF THE PREFERRED EMBODIMENTS

Figure 12:
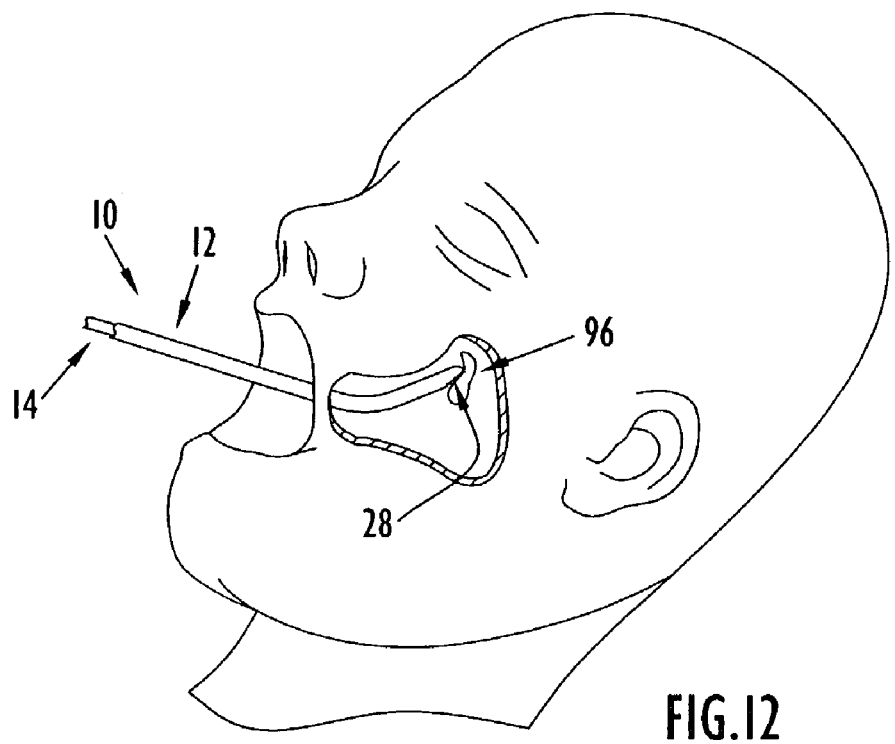
FIG. 12 depicts an adenoidectomy performed using the angled tissue cutting instrument of FIG. 1 in a T&A procedure.

The present invention relates to a straightening or unbending tool or apparatus for straightening or unbending an elongate angled member of an angled tissue cutting instrument and, in particular, the angled outer member of an angled tissue cutting instrument. As used herein, the terms "forward", "rearward", "inferiorly," "bottom," "downward," "superiorly," "top," "upward," "lateral," "side" and their derivatives are all relative terms that may vary depending on the orientations of the tools and the angled members and should not be construed as limitations to the features described thereby. The terms "angled", "bent" and "curved" and their derivatives are used synonymously, and the terms "straightening" and "unbending" and their derivatives are also used synonymously.

An angled tissue cutting instrument or blade 10 is illustrated in FIGS. 1 and 2 and includes an elongate angled outer tubular member 12 and an elongate inner member 14 rotatably or movably disposed within the outer member. Outer member 12, which may be considered an outer blade member, comprises a proximal end coupled to an outer member hub 16, a proximal length portion 18 of longitudinally or axially straight configuration extending distally from the outer member hub to an initial bend, curve or angle 20, and a distal length portion 22 extending distally from bend 20 to distal end 26. The distal length portion 22 is oriented at an angle A relative to the central longitudinal axis 24 of the proximal length portion and is of longitudinally or axially straight configuration extending distally from bend 20. The outer member 12 has an opening 28 therein adjacent distal end 26. The angle A is defined between a central longitudinal axis 30 of the distal length portion and the central longitudinal axis 24. The length of the distal length portion 22 from bend 20 to the distal end 26 may be considered as defining the working length of blade 10 and outer member 12. A forward aspect of the outer member 12 comprises distal length portion 22, bend 20, and at least part of the proximal length portion 18 extending from bend 20. The outer member 12 has a longitudinal profile along its forward aspect including angle A, the working length and the outer diameter of the outer member along the forward aspect.

The outer member 12 may comprise a rigid member formed by bending a continuous and unbroken tubular member of solid wall construction and uniform wall thickness, such that the initial bend 20 may be pre-formed therein as part of the fabrication or manufacturing process. Although the bent outer member 12 is essentially rigid, it is capable of being reverse bent to remove bend 20 therefrom when sufficient force is applied thereto. The orientation of opening 28, the angle, radius of curvature and location of bend 20, the working length, and the outer diameter of the outer member are dependent on the surgical procedure to be performed. The angled tissue cutting instrument 10 is particularly designed for use as an adenoid blade with the distal length portion 22 extending from bend 20 at an angle A of about 40 degrees relative to the central longitudinal axis 24, the bend 20 having a radius of curvature R of about 0.875 inch and a location about 0.7 inch from the distal end, and the opening 28 facing outwardly relative to the direction of the bend, i.e. relative to the center of curvature for the bend. The outer member 12 is typically made of a medically acceptable metal such as stainless steel.

Outer members 12 may be made available having different bend angles A, working lengths and/or outer diameters. Representative outer members having illustrative combinations of angles and outer diameters include an outer member having an angle A of 45° and an outer diameter of 4.5 mm, an outer member having an angle A of 60° and an outer diameter of 3.5 mm, an outer member having an angle A of 12° and an outer diameter of 4.0 mm, and an outer member having an angle A of 40° and an outer diameter of 4.0 mm. The representative outer members can have any suitable working lengths.

Inner member 14, which may be considered an inner blade member, may be tubular or non-tubular but is shown as being tubular in the case of instrument 10. Inner member 14 has a proximal length region 32 extending distally from an inner member hub 34, a distal end formed as or provided with a cutting tip 36 and a flexible or bendable region 38 between proximal length region 32 and cutting tip 36. The cutting tip 36 is adapted to cut anatomical tissue, and the cutting tip for inner member 14 includes an opening 40 communicating with a lumen 42 through the inner member and a cutting edge 44 along a peripheral edge of opening 40. The cutting edge 44 may be designed in various ways, for example as a sharp peripheral edge of opening 40 or as a plurality of cutting teeth along a peripheral edge of the opening 40 as shown for inner member 14. When the inner member 14 is disposed within the outer member 12 as shown in FIG. 1, the inner member extends through the outer member hub 16 with the inner member hub 34 disposed proximally of the outer member hub, the cutting edge 44 is exposed by the opening 28 of outer member 12, and the flexible region 38 is disposed within or adjacent the bend 20 so that the inner member follows or conforms to the longitudinally or axially bent, curved or angled configuration of the outer member. The proximal length region 32 is rigid and transmits torque from a powered surgical handpiece, shown at 84 in FIG. 6, via the flexible region 38 to rotate the cutting tip 36 when the inner member 14 is rotated relative to and within the outer member 12 by the powered surgical handpiece. The flexible region 38 allows the inner member 14 to conform to the angled configuration of the outer member 12 as it is rotated relative to and within the outer member. The hubs 16 and 34 are adapted to be removably coupled with the powered surgical handpiece, and the powered surgical handpiece may be of the type disclosed in U.S. Pat. No. 5,916,231 to Bays, the entire disclosure of which is incorporated herein by reference. Depending on the design of the angled tissue cutting instrument, the inner member may or may not be removable from the outer member.

The cutting tip 36 can have various configurations depending on the surgical procedure to be performed. The cutting tip 36 accesses anatomical tissue at an operative site via the opening 28 of outer member 12 and is aligned with or disposed adjacent the opening 28 as the inner member 14 is rotated with in the outer member 12. The outer member 12 can be provided with or without a cutting edge. In the case of instrument 10, the outer member 12 is shown as having a cutting edge 46 cooperable with the cutting edge 44 of inner member 14 to cut anatomical tissue as the inner member is rotated within the outer member. The cutting edge 46 may likewise be designed in various ways, for example as a sharp peripheral edge of opening 28 or as a plurality of cutting teeth along a peripheral edge of the opening 28 as shown in FIGS. 1 and 2. The cutting edge 44 moves past the cutting edge 46 as the inner member is rotated within the outer member to cut anatomical tissue. Anatomical debris may be aspirated from the operative site through the lumen 42 of inner member 14, the opening 40 of the inner member forming a suction inlet through which debris is aspirated. Where the powered surgical handpiece of the aforementioned Bays patent is used, the debris is aspirated through the inner member and the handpiece. The flexible region of the inner member can be formed in various ways, the flexible region 38 being formed by way of example of a reinforced polymeric material. The inner member 14 is made of a medically acceptable or biocompatible material such as stainless steel. For use as an adenoid blade, the angled tissue cutting instrument 10 may be a RADenoide Blade of Medtronic Xomed Surgical Products, as represented by U.S. Pat. No. 5,922,003 to Anctil et al, the entire disclosure of which is incorporated herein by reference. As described further below, the angled tissue cutting instrument may be a sinus blade such as the RAD® 40 Curved Blade or the RAD 60 X-TREME™ Curved Blade of Medtronic Xomed Surgical Products.

Aspiration may be accomplished in the angled tissue cutting instrument 10 through the inner member, through the outer member, such as between the outer member and the inner member, or in any other suitable manner. However, it should be appreciated that the angled tissue cutting instrument can be provided and/or used without aspiration. The angled tissue cutting instrument may be provided with or without an irrigation passage or channel for supplying irrigating or flushing fluid to the operative or cutting site and both aspiration and irrigation may be provided in the angled tissue cutting instrument. Irrigation may be provided along the instrument in various ways including through the inner member, through the outer member, such as between the outer member and the inner member, externally along the outer member, or in any other suitable manner. In the instrument 10, for example, the outer member hub 16 has an optional nipple 48 extending proximally from a side of the outer member hub at an acute angle relative to the central longitudinal axis 24 and communicating with an annular space between the outer member 12 and the inner member 14. When a source of irrigating or flushing fluid is connected with the nipple 48, the fluid will be supplied to the operative or cuffing site via the opening 28, for example to irrigate the site or clear blockages. The angled tissue cutting instrument may include an external irrigation channel as disclosed in U.S. Pat. No. 5,782,795 to Bays and U.S. No. 6,312,438 B1 to Adams, the entire disclosures of which are incorporated herein by reference. The Adams patent is also representative of a burr tip which may be used as the cutting tip in the angled tissue cutting instrument and of an aspiration passage and aspiration ports which may be incorporated in the inner member.

Although the straightening tool of the present invention is particularly desirable for use with a curved, bent or angled adenoid blade, as represented by the angled tissue cutting instrument 10 and by the RADenoid® Blade of Medtronic Xomed Surgical Products, and with a curved, bent or angled sinus blade as represented by the RAD 40® Curved Blade and RAD 60 X-TREME® Curved Blade of Medtronic Xomed Surgical Products, it should be appreciated that the straightening tool can be used or adapted for use with various other types of curved, bent or angled tissue cutting instruments of various manufacturers. In particular, the straightening tool can be adapted for use with laryngeal blades, as represented by the Skimmer Angle-Tip blades and the Tricut™ Angle-Tip blades of Medtronic Xomed Surgical Products, used by way of example for supraglottic and subglottic papilldma removal or debulking, tumor debulking, tracheal stenosis and trans-sphenoidal hypophysectomy.

A straightening or unbending tool or apparatus 50 according to the present invention is illustrated in FIGS. 3-6 and includes an unbending channel for unbending an elongate angled member, such as angled outer member 12, having a particular longitudinal profile along its forward aspect and a guide template for matching the angled member to the unbending channel. The straightening tool 50 is integrally, unitarily or monolithically formed as one piece with no moving parts and includes a handle 52 and a positioning block 54 extending from the handle. The handle 52 comprises an elongate cylindrical section 56 joined at one end thereof to a partial spherical cap 58 and joined at the opposite end thereof to positioning block 54. The cylindrical section 56 may be provided with external ridges or grooves, as shown in FIG. 3, to accommodate the fingers of a hand grasping the handle 52, and/or the handle may have various ergodynamic external configurations.

The positioning block 54 has an external surface comprised of external side walls 55a and 55b extending from handle 52 to an external forward end wall 62, and external top and bottom walls 57a and 57b extending from handle 52 to end wall 62. The side walls 55a and 55b may be planar and parallel to one another, and may be tangential to the circumference of cylindrical section 56 as shown for positioning block 54. The end wall 62 may be perpendicular to the external side walls 55a and 55b. The top and bottom walls 57a and 57b may each comprise a first or rearward top wall segment 59 extending angularly outwardly from the handle 52 to a second or forward top wall segment 61 extending from the first top wall segment 59 to end wall 62. The first top wall segments 59 may extend angularly outwardly in opposite directions to each other, and the second top wall segments 61 may be parallel to one another. The first and second top wall segments 59 and 61 may be outwardly curved or convex between side walls 55a and 55b as best shown in FIG. 5. Preferably, the positioning block 54 has blunt, rounded or smooth corners and edges. The positioning block 54 can have various external configurations other than the configuration shown in FIGS. 3-6 with an unbending channel 64 disposed within the positioning block and a guide template 66 disposed along an external wall of the positioning block.

The unbending channel 64 is within the positioning block 54 and comprises a confinement passage 68 and an unbending slot 70 extending from the confinement passage to an open end along end wall 62 presenting an exit opening of the unbending slot 70 along the external surface of the positioning block 54. The confinement passage 68 is bounded rearwardly by internal rearward or abutment wall 72, inferiorly by an internal confinement passage wall or bottom wall 74 and superiorly by an internal confinement passage wall or top wall 76. One side of the confinement passage 68 bounded laterally by internal side wall 78a extending between the bottom and top walls 74 and 76, while the opposite side of the confinement passage is open to the guide template 66. The bottom wall 74, which is planar, extends forwardly from abutment wall 72 to a contact surface 80 extending downwardly at an angle from bottom wall 74 to end wall 62. The top wall 76 extends forwardly from the abutment wall 72 to an internal upper wall 82 of the unbending slot 70, and the top wall 76 is planar and parallel to the bottom wall 74. The distance between the bottom and top walls 74 and 76 defines a confinement passage dimension selected to confinably receive, with a close fit, the outer diameter of the distal length portion 22 of the angled member 12 to be straightened using the unbending channel 64 of tool 50 as described further below. The confinement passage 68 may be coaxial with handle 52 as shown for tool 50 or may be non-coaxial therewith as shown for tool 150.

The unbending slot 70 extends from the confinement passage 68 to the open end or exit opening thereof along end wall 62. The unbending slot 70 is bounded laterally by opposing internal side walls 78a and 78b, inferiorly by an inferior internal wall or contact surface 80 and superiorly by an upper or superior internal wall 82. The side wall 78a extends from abutment wall 72 to end wall 62 while the side wall 78b extends from the confinement passage 68 to end wall 62. The side walls 78a and 78b are planar and parallel to one another. The contact surface 80 extends between the side walls 78a and 78b. The upper wall 82 comprises a curved or angled upper wall segment extending from the top wall 76 to a straight upper wall segment of upper wall 82 extending from the curved or angled upper wall segment to the open end of the unbending slot 70. The contact surface 80 is preferably curved between the side walls 78a and 78b to cradle the outer diameter of the angled member 12 during straightening or unbending thereof. The distance between the internal side walls 78a and 78b defines an unbending slot dimension selected to accommodate the outer diameter of the angled member 12 with a close fit while still allowing the proximal length portion 18 to be pivotally moved in the unbending slot 70 between the upper wall 82 and the contact surface 80 in a plane of pivotal movement coincident with a central longitudinal axis of the confinement passage 68 and in a direction opposite the initial bend 20 and relative to the distal length portion confinably received in the confinement passage. The unbending slot 70 has a dimension between the wall 82 and the contact surface 80 defining a range of pivotal movement for the proximal length portion of the angled member within the unbending slot 70 to effect straightening of the angled member 12 in response to pivotal movement of the proximal length portion 18 into contact with the contact surface 80 as explained below. In the case of tool 50, the unbending slot 70 and confinement passage 68 are bisected by the plane of pivotal movement, which is parallel to internal side walls 78a and 78b and coincident with the central longitudinal axis of the confinement passage 68. The open end or exit opening of unbending slot 70 extends along end wall 62 from contact surface 80 to the upper wall 82. In the case of tool 50, the upper wall 82 and the open end of slot 70 terminate along external top wall 57a so that the open end of slot 70 extends from end wall 62 some distance longitudinally along external top wall 57a. The length of the open end of slot 70 may vary in accordance with the angle of the angled member to be straightened by unbending channel 64 and the angle required for contact surface 80. Depending on the angle of the angled member, the open end of slot 70 need not extend along the external top wall and may be confined to end wall 62 as described and illustrated for unbending tool 150.

The guide template 66 comprises a guide slot or track having a longitudinally extending entry opening along the external surface of the positioning block 54 and communicating with the unbending channel 64. The entry opening for the guide slot of guide template 66 is disposed along the external side wall 55b. The guide slot extends from the unbending channel 64 to the entry opening in a direction transverse or perpendicular to the plane of pivotal movement for the proximal length portion of the angled member in the unbending slot 70. The entry opening of the guide slot defines a longitudinal profile that corresponds to or matches the longitudinal profile of the forward aspect of angled member 12, and the guide slot may have a uniform longitudinal cross-section from the entry opening to the unbending channel 64 corresponding to the longitudinal profile of the entry opening. As best shown in FIG. 3, the longitudinal profile of the entry opening for the guide slot of guide template 66 includes a first or forward length section 86 corresponding to or matching part of the proximal length portion 18 of outer member 12 extending from bend 20, a second or rearward length section 88 corresponding to or matching the distal length portion 22 of outer member 12 and a bent, curved or angled length section 90 joining the first and second length sections 86 and 88. The angled length section 90 corresponds to or matches the initial curve, bend or angle 20 of outer member 12. The guide slot terminates at one end at abutment wall 72, which extends in the transverse direction from the external side wall 55b to the internal side wall 78a and defines a closed end for the guide slot. The guide slot terminates at an opposite end at a transverse exit opening extending from the entry opening to the exit opening of the unbending slot 70.

The second length section 88 of the guide slot is bounded inferiorly by bottom wall 74 and superiorly by the top wall 76, the bottom and top walls 74 and 76 extending in the transverse or perpendicular direction from internal side wall 78a to the external side wall 55b. The first length section 86 and the angled length section 90 of the guide slot are bounded inferiorly by an internal lower wall 92, shown in FIG. 3, extending in the transverse or perpendicular direction from internal side wall 78b to external side wall 55b and are bounded superiorly by upper wall 82 which extends in the transverse or perpendicular direction from internal side wall 78a to external side wall 55b. The lower wall 92 is parallel to upper wall 82. The central longitudinal axis of the second length section 88 of the guide slot is disposed at angle A to the central longitudinal axis of the first length section 86 thereof such that the angled length section 90 has a bend angle that is the same as the bend angle A of the outer member 12. The guide slot has an upper surface comprising internal top wall 76 and internal upper wall 82, and a lower surface comprising internal bottom wall 74 and internal lower wall 92. The upper surface of the guide slot is parallel to the lower surface thereof, with the distance between the upper and lower surfaces of the guide slot being uniform from external side wall 55b to the unbending channel 64. The longitudinal profile of the entry opening of the guide slot closely corresponds to the longitudinal profile of the forward aspect of angled member 12, allowing the forward aspect of the outer member 12 to be introduced and positioned in the guide slot via the entry opening of the guide slot along external side wall 55b, with the proximal length portion 18 of the angled member 12 passing through the exit opening of the guide slot to the exterior of the positioning block 54 as represented in FIG. 3. It is preferred that the longitudinal profile of the entry opening of the guide slot match or correspond as close as possible to the longitudinal profile of the angled member 12 along its forward aspect to allow a complementary, mating or close fit between the forward aspect and the entry opening of the guide slot, while still allowing the forward aspect to be moved within and along the guide slot in the direction transverse or perpendicular to the plane of pivotal movement for the proximal length portion 18 in the unbending slot 70 for guided introduction of the forward aspect into the unbending channel 64 to effect straightening of the angled member 12 as described further below. The upper surface of the guide slot conforms to or follows the same longitudinal configuration or profile as the upper or conforming surface of the unbending channel 64 defined by the top wall 76 of confinement passage 68 and upper wall 82 of unbending slot 70.

The second length section 88 of the guide slot matches or corresponds in longitudinal profile to the distal length portion 22 of angled member 12, and the angled length section 90 of the guide slot has a bend, curve or angle that matches or corresponds in longitudinal profile to the initial bend 20 of the angled member 12. The first length section 86 of the guide slot matches or corresponds in longitudinal profile to at least part of the proximal length portion 18 of angled member 12 extending from bend 20. Accordingly, the longitudinal profile of the guide slot matches or corresponds to and is complementary to the longitudinal profile of the forward aspect of the angled member 12 including the angle A, the working length and the outer diameter of the angled member 12 along its forward aspect. The longitudinal profile of the guide slot is representative of the longitudinal profile of the unbending channel 64 in that the upper surface of the unbending channel is continuous with and follows the longitudinal configuration or profile of the upper surface of the guide slot while the bottom wall 74 of the confinement passage 68 is continuous with and defines the longitudinal configuration or profile of the lower wall of the guide slot along the second length section 88. Accordingly, when the distal length portion 22 of angled member 12 is disposed in the confinement passage 68 with distal end 26 in abutment with abutment wall 72, the distal length portion 22 is closely confined between walls 74 and 76, the bend 20 and proximal length portion 18 extend closely along the upper wall 82 of unbending slot 70, and the proximal length portion 18 exits or passes through the exit opening of unbending slot 70 to the exterior of the positioning block 54. The unbending channel 64 is thusly optimally designed for the longitudinal profile of angled member 12 including the particular bend angle, working length and outer diameter for angled member 12, with the contact surface 80 at the appropriate angle relative to the confinement passage 68 to effect striaghtening of the outer member after spring back as described further below. The guide template 66 corresponds to or is associated with with unbending channel 64, and its guide slot provides an external guide by which the angled member can be matched to the guide template and, therefore, to the unbending channel, so that the optimal unbending channel is used for unbending the angled member.

The contact surface 80 is angled from the bottom wall 74 of confinement passage 68 in a direction opposite the angle of upper wall 82 of unbending slot 70, the contact surface 80 being angled downwardly in opposition to the upwardly angled upper wall 82. The contact surface 80 forms an angle with the plane of bottom wall 74 as described in the application incorporated herein by reference, and this angle is selected to obtain straightening of angled member 12 after spring back in the direction of initial bend 20. The angle of contact surface 80 may be in the range of 5 to 7 degrees.

The straightening tool 50 is preferably made of a medically acceptable material, including metals, such as stainless steel, ULTEM, ABS, PEEK and LEXAN, for example, having sufficient strength to effect straightening or unbending of the angled member as explained further below. The straightening tool 50 may be fabricated by molding. The straightening tool 50 may be designed for sterilization to medical standards for repeated use or may be disposable after each use. The straightening tool 50 has no moving parts or inaccessible recesses such that proper sterilization is greatly facilitated. Various different straightening tools may be provided having various different unbending channels, respectively, and corresponding guide templates for various different angled members having forward aspects of various different longitudinal profiles. Alternatively, a single straightening tool may be provided with a plurality of various different unbending channels and guide templates corresponding thereto as explained below for straightening tool 150.

The guide template 66 can be used to match the forward aspect of the angled member 12 with the unbending channel 64 so that the appropriate unbending tool or channel is selected for unbending the angled member 12. Matching can be facilitated by placing the forward aspect of the angled member 12 alongside the entry opening of the guide slot of the guide template 66 with the distal length portion 22, the bend 20 and the proximal length portion 18 of the angled member aligned with the second length section 88, the angled length section 90 and the first length section 86 of the entry opening of the guide slot, respectively. The angled member 12 can also be introduced in the guide slot with a complementary, close or mating fit through the entry opening thereof along external wall 55*b* to confirm proper matching. When the forward aspect is introduced in the guide slot, the proximal length portion 18 of the angled member 12 will extend externally of the positioning block 54 from the exit opening of the guide slot.

When it is desired to straighten or unbend angled member 12 using tool 50 properly matched thereto, the angled member can be placed in the unbending channel 64 by first introducing the forward aspect of the angled member in the guide slot through the entry opening of the guide slot along external wall 55*b* and then moving the angled member along the guide slot in the direction transverse or perpendicular to the plane of pivotal movement for the proximal length portion within the unbending slot 70, as permitted by the exit opening of the guide slot, to guidedly introduce and position the forward aspect in the unbending channel. The guide slot guides the forward aspect into the unbending channel 64 so that the distal end 26 of angled member 12 abuts abutment wall 72 with the distal length portion 22 confined in confinement passage 68, the bend 20 disposed adjacent the confinement passage in unbending slot 70, and the proximal length portion 18 extending closely along upper wall 82 to pass through the exit opening of the unbending slot to the exterior of the positioning block 54 as shown in FIG. 6. By guiding the forward aspect of the angled member 12 into the unbending channel 64, the guide template 66 and its slot ensure that the forward aspect is correctly positioned in the unbending channel. In addition, the forward aspect of the angled member 12 can be visualized in the unbending channel via the entry opening of the guide slot along external wall 55*b* to confirm proper positioning. The forward aspect of the angled member 12 can be placed in the unbending channel 64 simultaneously with matching the angled member to the guide template 66 by first placing the forward aspect in the guide slot to confirm the correct match and then moving the forward aspect along the guide slot and into the unbending channel. Alternatively, the angled member 12 matched to the guide template 66 can be positioned in the unbending channel 64 by introducing the distal end 26 of the angled member directly into the unbending slot 70 via its exit opening and moving the angled member longitudinally until the distal end 26 abuts abutment wall 72.

In a method of straightening or unbending the angled tissue cutting instrument 10 using the straightening tool 50, the angled member 12 is first compared to the guide template 66 and, in the event that the angled member indeed matches the guide template, is then positioned in the unbending channel corresponding to or associated with the matching guide template. Where the angled member does not match the guide template, as where the forward aspect of the angled member fails to visually match and/or physically mate with or complementary fit within the entry opening of the guide slot, the associated unbending channel is rejected for use in straightening the angled member. The forward aspect of the angled member is then compared to one or more other different guide templates of the same or a different straightening tool or tools until a correct match is established between the forward aspect and the guide slot of a guide template, and the forward aspect is positioned in the unbending channel corresponding to the matching guide template.

Matching the angled member to the correct guide template and positioning the forward aspect in the unbending channel corresponding to the matching guide template can be executed by a single person using one hand to grasp the handle of the tool and the other hand to manipulate the angled member. The angled outer member 12 can be matched to a guide template and positioned in the associated unbending channel with the inner member 14 withdrawn from the angled outer member, where the design of the instrument permits withdrawal or removal of the inner member from the outer member as shown by solid lines in FIG. 6, or with the inner member 14 disposed within the outer member 12 as shown in dotted lines in FIG. 6. The inner and outer members may be uncoupled from the powered surgical handpiece 84 prior to matching and/or positioning, or the inner and outer members may remain coupled to the powered surgical handpiece 84 during matching and/or positioning as also shown in FIG. 6.

When the angled member 12 is positioned in the unbending channel 64 with distal end 26 in abutment with abutment wall 72, the outer or external diameter of the angled member is received in the confinement passage 68 with a close fit, and the distal length portion 22 is confined against radial movement, i.e. movement in a direction radial to its central longitudinal axis 30. The distal length portion 22 of the angled member is thusly coaxially aligned with the confinement passage, and the bend 20 and part of the proximal length portion 18 are disposed in unbending slot 70 along the upper surface of the unbending channel 64. The bend 20 is not confined in the confinement passage 68, and the proximal length portion 18 extends upwardly from the bend 20 relative to the distal length portion 22 and extends exteriorly of the positioning block 54 through the open end or exit opening of unbending slot 70. Of course, the straightening tool 50 and angled member 12 may be inverted 180° or otherwise rotated for use in a position other than the position shown in FIGS. 3 and 6.

Once the distal length portion 22 of angled member 12 is positioned in the unbending channel 64 and confined in the confinement passage 68 with the distal end 26 in abutment with the abutment wall 72, the proximal length portion 18 of angled member 12 that extends externally or exteriorly from the exit opening of unbending slot 70 is forcefully moved, pivoted or rotated, typically manually with the hand, in a the plane of pivotal movement and in the direction opposite the bend 20, i.e. downwardly looking at FIG. 6, until the proximal length portion 18 contacts or abuts the contact surface 80 to reverse bend the member 12 as shown in dotted lines in FIG. 6. Reverse bending the member 12 imparts a positive bend angle to the member 12 opposite the initial bend 20. As the proximal length portion 18 is pivoted into contact with contact surface 80, it is confined between the internal side walls 78a and 78b of the unbending slot against movement transverse to the plane of pivotal movement to prevent misalignments and distortion. The contact surface 80 limits pivotal movement of the proximal length portion 18 in the plane of pivotal movement in the unbending slot 70, and the curved configuration of the contact surface 80 mates with the external or outer curvature of the member 12 to ensure proper abutment of the member 12 with the contact surface. The constraint provided by the confinement passage 68 acts as a fulcrum about which the member 12 is pivoted without damaging the opening 28 and/or the cutting edge 46 thereof. Where the inner member 14 is disposed within the angled outer member 12 during straightening, the flexible region of the inner member allows the inner member to follow or conform to the configuration of the outer member during straightening, and the cutting edge and/or opening of the inner member is also not damaged.

Once the proximal length portion 18 has been moved into contact with contact surface 80, pivoting force or pressure on the proximal length portion in the direction opposite the initial bend 20 is released, and the proximal length portion will spring back a small predictable or estimatable amount away from contact surface 80 in the direction of the initial bend, as shown in dotted lines and by the arrow in FIG. 6, due to the spring memory characteristics of the angled member. The unbending slot 70 and, in particular, the side walls 78a and 78b thereof, confine the angled member 12 against movement transverse to the direction of spring back movement such that proper alignment is maintained. The dimension of the unbending slot 70 in the plane of pivotal movement for the proximal length portion 18 therein and the angle of contact surface 80 ensure that the member 12, after springing back from contact surface 80, assumes a longitudinally or axially straight configuration in which the member 12 is completely longitudinally or axially straight as shown in dotted lines in FIG. 6 or is substantially completely longitudinally or axially straight with only a slight positive bend, curve or angle in the same direction as the initial bend. Accordingly, "unbending" and "straightening" as used herein refer to a complete unbending or straightening in which the angled member is rendered completely longitudinally or axially straight or a substantially complete unbending or straightening in which the angled member is rendered substantially completely longitudinally or axially straight. The extent to which the proximal length portion 18 springs back and, therefore, the size of any residual positive bend, curve or angle, will depend on the spring memory characteristics of the particular angled member.

Straightening or unbending of the angled member 12 is accomplished using the straightening tool 50 in a minimal number of simple procedural steps. Once straightening has been accomplished, the angled member need only be withdrawn from the tool by pulling the angled member away from the straightening tool in the longitudinal or axial direction. If necessary, the straightened angled member is reassembled with the inner member to form a longitudinally or axially straight tissue cutting instrument, and the reassembled inner and outer members are reattached to the powered surgical handpiece. Of course, where the powered surgical handpiece 84 remains attached to the inner and outer members during straightening, the longitudinally straight tissue cutting instrument is ready for further use upon withdrawal from the straightening tool.

An alternative straightening or unbending tool 150 is depicted in FIGS. 7-11 and is characterized by a plurality of different unbending channels each having a guide template. The tool 150 comprises handle 152, a first positioning block 154 extending from handle 152 in a first direction and a second positioning block 154' extending from handle 152 in a second direction opposite the first direction. Handle 152 comprises an elongate cylindrical section 156 extending between the first and second positioning blocks 154, 154' and provided with external ridges or grooves to facilitate grasping. The positioning blocks 154 and 154' are similar to positioning block 54 except that positioning block 154 has two unbending channels 164a and 164b therein and positioning block 154' has two unbending channels 164a' and 164b' therein. Although each positioning block of tool 150 is shown with two unbending channels, it should be appreciated that each positioning block 154 and 154' could be provided with one or more unbending channels. The unbending channels 164a, 164b, 164a' and 164b' are similar to unbending channel 64 but are different from each other since the unbending channels 164a, 164b, 164a' and 164b' are designed for different angled members 112a, 112b, 112a' and 112b', respectively, having different longitudinal profiles along their forward aspects. Tool 150 has a guide template for each unbending channel, the tool 150 having guide templates 166a, 166b, 166a' and 166b' corresponding to the unbending channels 164a, 164b, 164a' and 164b', respectively. The guide templates 166a, 166b, 166a' and 166b' are similar to guide template 66 but are different from each other in accordance with the different longitudinal profiles of angled members 112a, 112b, 112a' and 112b', respectively.

The guide template 166a for unbending channel 164a is disposed along external sidewall 155a of positioning block 154 and has a longitudinal profile corresponding, matching or complementary to the longitudinal profile of the forward aspect of angled member 112a having by way of example an outer diameter of 4.0 mm and a bend angle A of 12°. Also, the confinement passage 168a of unbending channel 164a and the second length section of guide template 166a have a length corresponding to the working length of angled member 112a, and the upper surface of unbending channel 164a follows the longitudinal profile of the forward aspect. The unbending channel 164a conforms to the longitudinal profile of the guide template 166a as explained above for unbending channel 64 and guide template 66. The contact surface 180a for unbending channel 164a extends at an angle to the confinement passage 168a, and the angle is selected to reverse bend angled member 112a an amount sufficient to straighten outer member 112a after spring back. The guide template 166a communicates with the unbending channel 164a as described above for guide template 66 and unbending channel 64.

The guide template 166b for unbending channel 164b is disposed along external side wall 155b of positioning block 154 and has a longitudinal profile corresponding to the longitudinal profile of the forward aspect of angled member 112b having by way of example an outer diameter of 4.5 mm and a bend angle A of 45°. Also, the confinement passage 168b of unbending channel 164b and the second length section of guide template 166b have a length corresponding to the working length of angled member 112b. As best seen in FIG. 9, the guide template 166b is longer than guide template 166a. The contact surface 180b for unbending channel 164b extends at an angle from confinement passage 168b, and the angle of contact surface 180b is selected to reverse bend angled member 112b an amount sufficient to straighten outer member 112b after spring back. The unbending channel 164b conforms to the longitudinal profile of the guide template 166b, with the upper surface thereof following the longitudinal profile of the forward aspect of angled member 112b. The unbending channels 164a and 164b are disposed side by side in the positioning block 154 in parallel arrangement, with the planes of the unbending channels 164a and 164b being laterally offset on opposite sides of a central longitudinal axis of tool 150 as best seen in FIG. 10.

The guide template 166a' for unbending channel 164a' is disposed along external side wall 155a' of positioning block 154' and has a longitudinal profile corresponding to the longitudinal profile of a forward aspect of angled member 112a' having an outer diameter of 4.0 mm and a bend angle A of 40°. Also, the confinement passage 168a of unbending channel 164a' and the second length section of guide template 166a' have a length corresponding to the working length of angled member 112a', and the upper surface of unbending channel 164a' conforms to the longitudinal profile of guide template 166a' as well as the longitudinal profile of the forward aspect of angled member 112a'. The contact surface 180a' for unbending channel 164a' extends at an angle to the confinement passage 168a', and this angle is selected to reverse bend angled member 112a' an amount sufficient to straighten angled member 112a' after spring back.

The guide template 166b' for unbending channel 164b' is disposed along external side wall 155b' of positioning block 154' and has a longitudinal profile corresponding to the longitudinal profile of a forward aspect of angled member 112b' having an outer diameter of 3.5 mm and a bend angle A of 60°. The confinement passage 168b' for unbending channel 164b' and the second length section of guide template 166b' have a length corresponding to the working length of angled member 112b'. The unbending channel 164b' conforms to the longitudinal profile of the guide template 166b', with the upper surface of the unbending channel 164b' following the longitudinal profile of the forward aspect of angled member 112b'. The contact surface 180b' for unbending channel 164b' extends at an angle to the confinement passage 168'. The angle of the contact surface 180b' is selected to reverse bend angled member 112b' an amount sufficient to straighten angled member 112b' after spring back. As shown in FIG. 9, the positioning block 154' is representative of a positioning block in which both unbending channels 164a', 164b' and the guide templates 166a', 166b' therefor are substantially the same length. The unbending channels 164a' and 164b' are arranged in positioning block 154' similar to the arrangement of unbending channels 164a and 164b in positioning block 154.

The unbending tool 150 is used in a manner similar to that described for tool 50 in that the guide templates 166a, 166b, 166a' and 166b' may be used to match the angled members 112a, 112b, 112a' and 112b' with the appropriate unbending channels 164a, 164b, 164a' and 164b, respectively, prior to straightening by visually comparing the longitudinal profiles of the forward aspects of the angled members with the guide templates and/or by positioning the forward aspects of the angled members in the guide templates with a complementary, mating or close fit. Accordingly, an individual straightening tool can be used to straighten various different angled members having different longitudinal profiles including different outer diameters, bend angles and/or working lengths, and the guide templates ensure that each angled member is matched to the appropriate unbending channel. The straightening tool 150 may be used to match the forward aspect of an angled member of an angled tissue cutting instrument with a guide template of the straightening tool and thereafter unbend or straighten the angled member using the unbending channel corresponding to the matching guide template as explained above. The step of matching the forward aspect of the angled member with the guide template may include a visual side-by-side comparison without inserting the forward aspect in the guide template but will preferably include placing the forward aspect within the guide template and thereafter moving the forward aspect along the guide template into the associated unbending channel.

The straightening procedure may be performed during a surgical procedure wherein an angled tissue cutting instrument and a straightening tool 50, 150 having a guide template matching the angled member of the instrument are provided as a tissue cutting instrument system or apparatus. Matching of the angled member to the guide template is accomplished as described above. The angled tissue cutting instrument is used during the surgical procedure to remove anatomical tissue at an operative site, the angled tissue cutting instrument is subsequently straightened or unbent during the surgical procedure to obtain a longitudinally or axially straight tissue cutting instrument, and the straight tissue cutting instrument is thereafter used in the surgical procedure to further remove anatomical tissue. By using an angled tissue cutting instrument in which the outer angled member is supplied with a manufactured pre-formed bend, the instrument is ready for use without any bending of the outer member being needed to impart an angle thereto prior to performing the surgical procedure.

Figure 13:
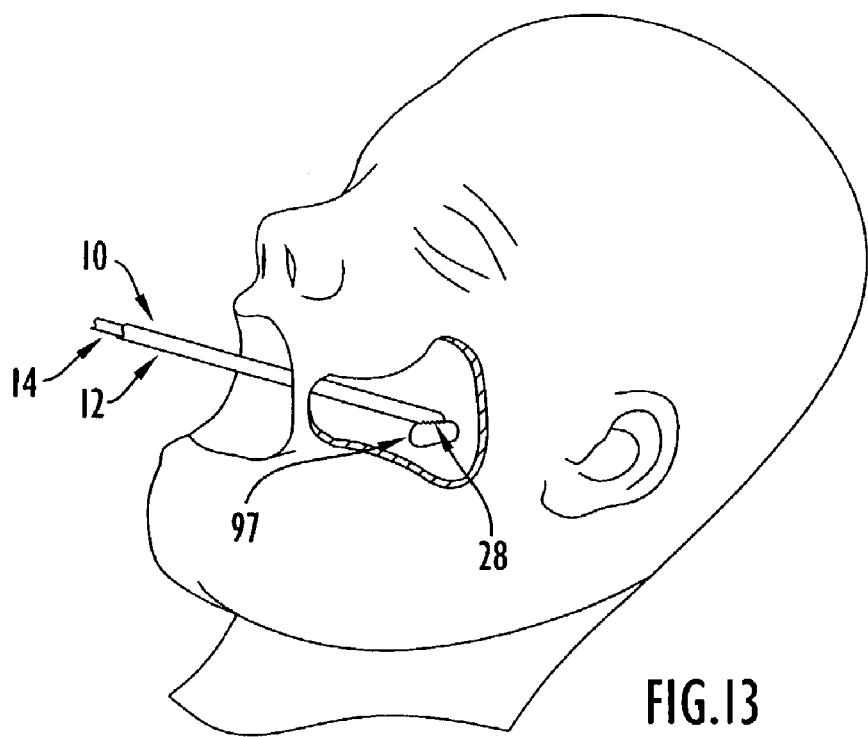
FIG. 13 shows a straight tissue cutting instrument obtained by matching the angled tissue cutting instrument of FIG. 1 to the guide template of the straightening tool of FIG. 3 and straightening the angled tissue cutting instrument using the unbending channel of the straightening tool corresponding to the matching guide template subsequent to the adenoidectomy, and depicts use of the straight instrument to perform a tonsillectomy in the T&A procedure.

FIGS. 12 and 13 are illustrative of a surgical procedure, particularly a combined tonsillectomy and adenoidectomy (T&A) procedure, using a tissue cutting instrument system including the angled tissue cutting instrument 10 and the straightening tool 50. FIG. 12 illustrates the angled tissue cutting instrument or adenoid blade 10 inserted through a patient's mouth to perform an adenoidectomy. The distal end of the angled tissue cutting instrument 10 is introduced into the nasopharynx with the opening 28 facing an adenoid 96. The adenoidectomy is initiated in the anterior nasopharynx, near the choana. The inner member 14 is rotated within the outer member 12 by the powered surgical handpiece 84, and the cutting edges 44 and 46 remove adenoid tissue. Removal of adenoid tissue is initiated using a light touch with the adenoid blade, with tissue removal being accomplished by moving the blade side-to-side and/or sweeping the blade anterior to posterior. Sweeping the blade anteriorly to posteriorly is particularly effective along the torus tubarius. The adenoid blade is predictably sharp for every case, allowing a precise progressive removal of adenoid tissue while simultaneous suction or aspiration evacuates blood and tissue from the operative site for enhanced visualization. Tissue at the superior choana and along the torus tubarius can be shaved away to effect a more thorough adenoidectomy which minimizes the potential for tissue regrowth and symptom recurrence. Continuous suction through the inner member keeps the surgical field visible while tissue is removed from difficult areas such as the superior choana and along the posterior torus tubarius. The precise shaving action of the adenoid blade removes well-defined portions of tissue exactly where the blade is placed. The increased surgical accuracy allows easy removal of hypertrophic adenoid tissue from the posterior nasal cavity and along the torus. The curved, bent or angled configuration of the adenoid blade greatly enhances access to the operative site.

Upon completion of the adenoidectomy, the instrument 10 is withdrawn from the patient's mouth, and the outer member 12 is compared to the guide template 66 to confirm proper matching as described above. Initial matching of the outer member to the guide template may be performed prior to surgery. The straightening tool 50 will be sterile so that the instrument 10 is not contaminated. The outer member 12 is straightened or unbent using the unbending channel associated with the matching guide template as described above to obtain a longitudinally or axially straight tissue cutting instrument 10. Given the fail-safe manner in which matching is accomplished, use of the most appropriate unbending channel is assured. The straight tissue cutting instrument 10 is inserted in the patient's mouth to perform a tonsillectomy as shown in FIG. 13. The opening 28 of the outer member 12 is positioned adjacent a tonsil 97, and the straight longitudinal profile of the tissue cutting instrument 10 enhances access to the tonsil 97. The inner member 14 is rotated within the outer member 12 via the powered surgical handpiece 84, and the cutting edges 44 and 46 remove anatomical tissue of the tonsil while suction or aspiration is effected through the inner member 14. Upon completion of the tonsillectomy, the straight tissue cutting instrument 10 is withdrawn from the patient's mouth.

Figure 14:
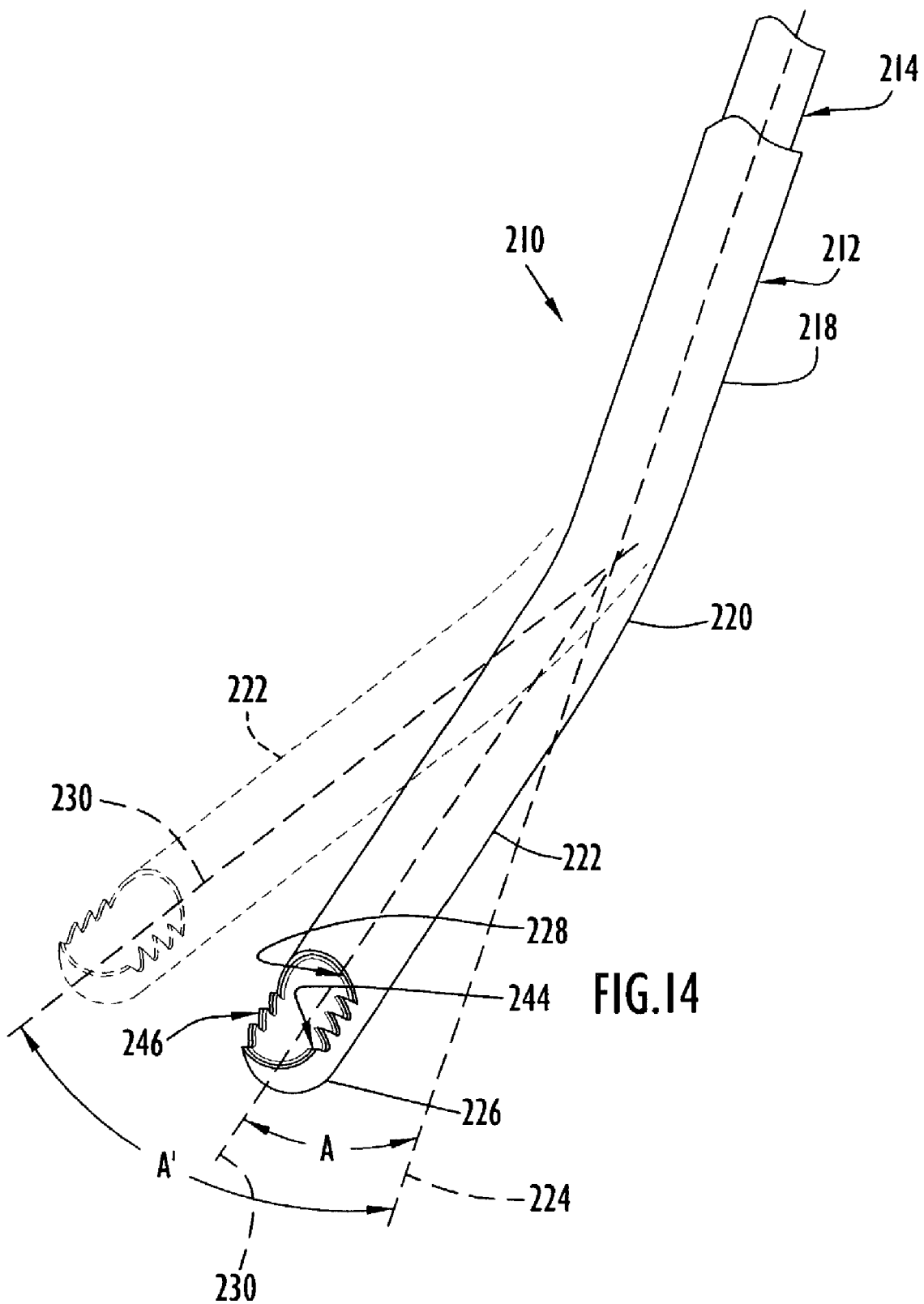
FIG. 14 is a broken perspective view of an alternative angled tissue cutting instrument or blade.

An alternative angled tissue cutting instrument 210 for use with straightening tools 50, 150 is shown in FIG. 14. Instrument 210 is similar to instrument 10 except that the opening 228 of outer member 212 faces in the direction of the center of curvature for bend 220. The angled tissue cutting instrument 210 corresponds to the RAD® 40 Curved Blade of Medtronic Xomed Surgical Products and has an angle A of about 40° between the central longitudinal axis 224 of proximal length portion 218 and the central longitudinal axis 230 of distal length portion 222. The angled tissue cutting instrument 210 may be provided with an angle A' of about 60° between the central longitudinal axis 224 of proximal length portion 218 and the central longitudinal axis 230 of distal length portion 222 as shown in dotted lines in FIG. 14 and as corresponds to the RAD 60 X-TREME™ Curved Blade of Medtronic Xomed Surgical Products. The angled tissue cutting instrument 210 is particularly advantageous for use as a sinus blade in sinus surgery to access the frontal recess and maxillary sinus, for ethmoid and frontal recess surgery, maxillary polyp removal, uncinectomy and antrostomy, for example. Depending on whether the angle A of outer member 212 is 40° or 60°, the outer member 212 may be straightened using the unbending channels 164a' or 164b' of tool 150 as determined via matching of the longitudinal profile of the forward aspect of angled member 212 with the correct guide template as described above.

Figure 15:
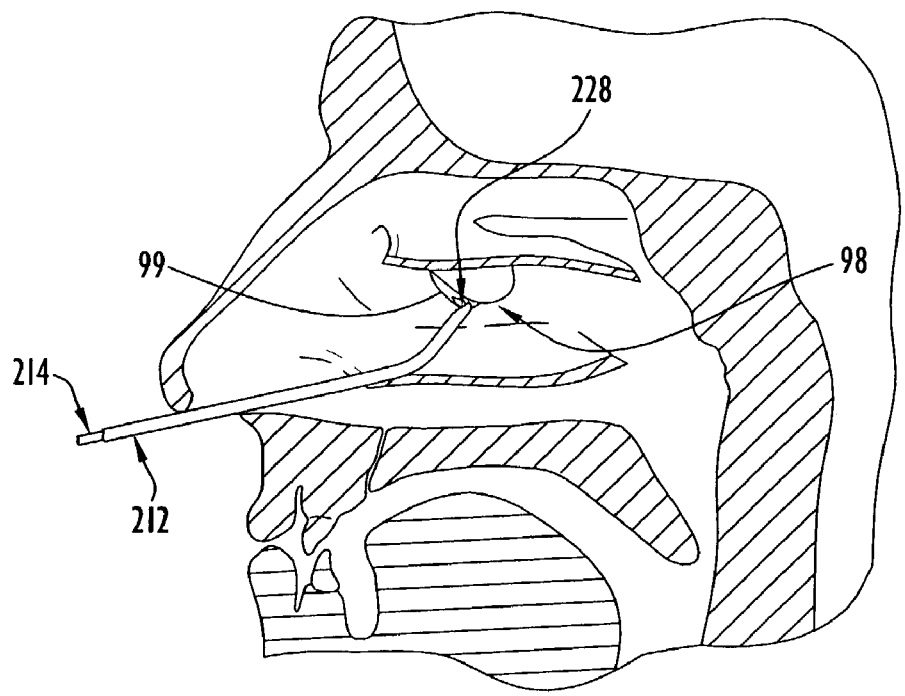
FIG. 15 depicts removal of sinus tissue using the angled tissue cutting instrument of FIG. 14 during a sinus procedure.
Figure 16:
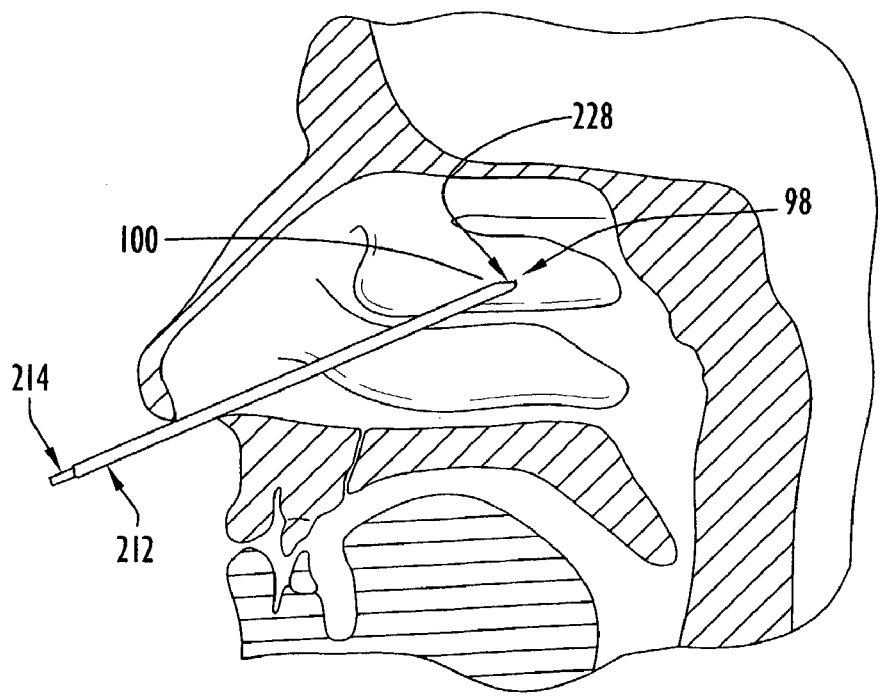
FIG. 16 shows a straight tissue cutting instrument obtained by matching the angled tissue cutting instrument of FIG. 14 to the matching guide template of the alternative straightening tool of FIG. 7 and straightening the angled tissue cutting instrument using the unbending channel of the alternative straightening tool corresponding to the matching guide template subsequent to removal of sinus tissue therewith, and depicts use of the straight instrument to further remove sinus tissue during the sinus procedure.

FIGS. 15 and 16 depict a surgical procedure including a sinus procedure performed using a tissue cutting instrument system or apparatus comprising angled tissue cutting instrument or sinus blade 210 and straightening tool 150. As shown in FIG. 15, the angled tissue cutting instrument 210 is introduced in a patient's nostril to position the opening 228 of outer member 212 adjacent anatomical tissue to be removed in the sinus. As an example, the opening 228 is shown positioned in the maxillary sinus 98, access to which is facilitated by the angled longitudinal configuration or profile of the blade. The inner member 214 is rotated within the outer member 212 via the powered surgical handpiece 84, and the cutting edges 244 and 246 are used to remove anatomical tissue of the maxillary sinus. Suction or aspiration may be accomplished through the inner member 214 as described above for angled tissue cutting instrument 10. The angled tissue cutting instrument 210 is then removed from the patient's nostril and is straightened using the unbending channel of tool 150 corresponding to the guide template of tool 150 that has been matched to the longitudinal profile of outer member 212 along its forward aspect. The thusly straightened tissue cutting instrument 210 is inserted in the patient's nostril as depicted in FIG. 16, and the inner member 214 is rotated within the outer member 212 to remove additional sinus tissue 100 in the sinus with the cuffing edges 244 and 246. When tissue removal using the straightened tissue cutting instrument 210 is complete, the instrument 210 is removed from the nostril.

In order to enhance the precision, control and efficacy of unbending the angled member of an angled tissue cutting instrument, it is advantageous for the confinement passage to be designed to receive the outer diameter of the angled member with a snug or close fit, for the outer diameter of the angled member to be closely confined between the internal side walls of the unbending slot, and for the length of the confinement passage to closely correspond to the working length of the angled member. In addition, it is preferred that the angle of the contact surface be selected in accordance with the bend angle and/or spring properties of the angled member, making it desirable to provide contact surfaces at different angles for angled members of different initial bend angles and/or spring back properties to effect complete straightening of the angled members or as close as possible to a complete straightening after spring back. Given the potential for numerous different angled tissue cutting instruments having outer members of different outer diameters, working lengths and/or bend angles, it is desirable to provide an unbending channel optimally designed for unbending an angled member of particular bend angle, outer diameter, working length and/or spring properties.

The guide templates ensure a correct match between a particular angled member and an optimal unbending channel therefor, and correct matching is facilitated since the longitudinal profiles of the guide templates correspond to the actual longitudinal profiles of the angled members undergoing comparison or matching with the guide templates. Angled members are straightened or unbent with greater precision, accuracy and control since each angled member may be straightened using the optimal unbending channel for the particular angled member. Each unbending channel may have its contact surface oriented at the optimal angle for straightening the particular angle member while accounting for spring back of the angled member. The guide templates communicate with the corresponding unbending channels and the properly matched angled members can be positioned in the unbending channels through the guide templates for ease of use and to ensure proper positioning of the angled members in the unbending channels. The angled members cannot be inserted through their corresponding guide templates in anything but the correct position and orientation, thereby eliminating trial and error positioning and incorrect unbending. A single unbending tool can be used to straighten a plurality of angled members having different longitudinal profiles.

In accordance with the present invention, various types of angled tissue cutting instruments can be straightened including rotary tissue cutting instruments as shown herein as well as oscillatory and reciprocatory tissue cutting instruments with or without an aspiration passage and with or without an irrigation passage. Angled tissue cutting instruments may be straightened using a minimal number of simple procedural steps capable of being performed by one person without extraneous equipment and in a brief amount of time. The ease, rapidity and accuracy with which angled tissue cutting instruments can be straightened may make it more desirable and advantageous to straighten an angled tissue cutting instrument during a surgical procedure for further use in the surgical procedure as a longitudinally straightened tissue cutting instrument rather than switching from an angled tissue cuffing instrument to another different longitudinally straight tissue cutting instrument. The outer members of the angled tissue cutting instruments can be straightened with the inner members withdrawn therefrom, the inner members disposed therein and with or without the powered surgical handpiece coupled with the inner and outer members. The openings in the outer members and the cutting edges, where provided in the outer member, are not damaged as a result of straightening. The openings and/or cuffing edges of the inner members are also not damaged where the inner members remain within the outer members during straightening. Proper positioning of the angled members in the unbending channels is easily accomplished by abutment of the distal ends of the angled members with the abutment walls and proper positioning is facilitated by inserting the angled members into the unbending channels via the guide templates. Straightening of the angled members is effected without deformation, kinking and/or misalignments, since the angled members are constrained by the confinement passages and guided by the unbending slots. Straightening of the outer members is controlled via abutment of the proximal length portions with the contact surfaces such that trial and error adjustments are not necessary. The straightening tools are sterilizable for repeated use or may be disposable for single patient use. The straightening tools are without moving parts and small recesses such that the effectiveness and reliability of sterilization is enhanced. Surgical procedures in which it is desirable to employ both angled and straight tissue cutting instruments are facilitated. Use of the most optimal blade configurations as well as the most optimal distal end cutting configurations for tissue removal during surgical procedures is promoted. The cost and time for surgical procedures and the required number of tissue cutting instruments for surgical procedures may all be reduced. The straightening tools are particularly advantageous for use in T&A procedures, sinus procedures and laryngeal procedures but may be used to straighten angled tissue cutting instruments in other surgical procedures. In the methods of the present invention, suction and/or irrigation may be accomplished via the tissue cutting instruments.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A straightening tool for straightening an elongate angled member of an angled tissue cutting instrument in which the elongate angled member has a proximal length portion and an initial bend connecting the proximal length portion to a distal length portion extending from the bend to a distal end, comprising a positioning block attached to a handle, said positioning block having an external surface;

an unbending channel within said positioning block including a confinement passage for confinably receiving the distal length portion of the elongate angled member and an unbending slot extending from said confinement passage to an exit opening of said unbending slot disposed along said external surface to accommodate passage of the proximal length portion of the angled member through said exit opening to the exterior of said positioning block, said unbending slot having a dimension between superior and inferior internal walls of said positioning block defining a range of pivotal movement for the proximal length portion of the angled member within said unbending slot in a plane of pivotal movement coincident with a central longitudinal axis of said confinement passage and in a direction opposite the initial bend and relative to the distal length portion confinably received in said confinement passage to effect straightening of the elongate angled member; and a guide template associated with said unbending channel and comprising a guide slot within said positioning block extending from said unbending channel in a direction transverse to said plane of pivotal movement to an entry opening of said guide slot disposed along said external surface of said positioning block, said entry opening defining a longitudinal profile that matches the longitudinal profile of a forward aspect of the elongate angled member extending from the distal end to proximally of the bend prior to straightening, said guide slot having an exit opening along said external surface of said positioning block extending from said entry opening to said exit opening of said unbending slot to allow the forward aspect of the elongate angled member to be introduced in said guide slot through said entry opening with the proximal length portion of the angled member passing through said exit opening of said guide slot to the exterior of said positioning block and to allow the forward aspect of the angled member to be moved alone said guide slot in said direction transverse to said plane of pivotal movement for guided introduction of the forward aspect into said unbending channel prior to straightening of the angled member.

2. The straightening tool recited in claim 1 wherein said longitudinal profile of said entry opening is matable with the longitudinal profile of the forward aspect of the angled member in a complementary close fit.

3. The straightening tool recited in claim 1 wherein said longitudinal profile of said entry opening comprises a first length section matching part of the proximal length portion extending from the bend, an angled length section matching the bend, and a second length section matching the distal length portion, said first length section being in communication with said exit opening of said guide slot.

4. The straightening tool recited in claim 3 wherein the proximal length portion and the distal length portion of the elongate angled member are straight, said first length section is straight to match the part of the proximal length portion, and said second length section is straight to match the distal length portion.

5. The straightening tool recited in claim 3 wherein said confinement passage is defined between a pair of internal confinement passage walls of said positioning block disposed in spaced relation to confine the distal length portion of the angled member against movement radial to a central longitudinal axis of the distal length portion, said confinement passage walls defining said second length section of said longitudinal profile of said entry opening.

6. The straightening tool recited in claim 5 wherein said confinement passage terminates at an abutment wall within said positioning block for abutment with the distal end of the elongate angled member within said confinement passage, said abutment wall extending between said confinement passage walls and defining a closed end of said guide slot.

7. The straightening tool recited in claim 5 wherein said inferior internal wall comprises a contact surface extending angularly from one of said confinement passage walls to said exit opening of said unbending slot, said contact surface limiting pivotal movement of the proximal length portion of the elongate angled member within said unbending slot in said plane of pivotal movement and in the direction opposite the initial bend and relative to the distal length portion confined in said confinement passage, to effect straightening of the angled member in response to pivotal movement of the proximal length portion into contact with said contact surface.

8. The straightening tool recited in claim 1 wherein said guide slot has a uniform longitudinal cross-section from said entry opening to said unbending channel corresponding to said longitudinal profile of said entry opening.

9. The straightening tool recited in claim 1 wherein said guide slot extends from said unbending channel to said entry opening in a direction perpendicular to said plane of pivotal movement.

10. The straightening tool recited in claim 1 comprising a plurality of said unbending channels within said positioning block to effect straightening of a plurality of elongate angled members including forward aspects having different longitudinal profiles, respectively, and a plurality of said guide templates associated with said unbending channels, respectively, and comprising respective ones of said guide slots within said positioning block having entry openings defining longitudinal profiles that match the different longitudinal profiles, respectively, of the forward aspects of the plurality of elongate angled members prior to straightening.

11. The straightening tool recited in claim 10 comprising two of said unbending channels and two of said guide templates associated with said unbending channels, respectively.

12. The straightening tool recited in claim 11 wherein said external surface of said positioning block comprises a pair of parallel external walls in opposed relation and said entry openings of said guide slots are disposed along said external walls, respectively.

13. The straightening tool recited in claim 1 wherein said positioning block is a first positioning block, said unbending channel is a first unbending channel to effect straightening of a first elongate angled member, said guide template is a first guide template, and further comprising a second one of said positioning blocks attached to said handle, a second one of said unbending channels within said second one of said positioning blocks to effect straightening of a second elongate angled member including a forward aspect having a longitudinal profile different from the longitudinal profile of the first elongate angled member, and a second one of said guide templates associated with said second one of said unbending channels and comprising a second one of said guide slots within said second one of said positioning blocks, said entry opening of said second one of said guide slots being disposed along said external surface of said second one of said positioning blocks and having a longitudinal profile that matches the longitudinal profile of the forward aspect of the second elongate angled member prior to straightening.

14. The straightening tool recited in claim 13 comprising a third one of said unbending channels within said first positioning block to effect straightening of a third elongate angled member including a forward aspect having a longitudinal profile different from the longitudinal profiles of the first and second elongate angled members, and a third one of said guide templates associated with said third one of said unbending channels and comprising a third one of said guide slots within said first positioning block, said entry opening of said third one of said guide slots being disposed along said external surface of said first positioning block and having a longitudinal profile that matches the longitudinal profile of the forward aspect of the third elongate angled member prior to straightening, and a fourth one of said unbending channels within said second one of said positioning blocks to effect straightening of a fourth elongate angled member including a forward aspect having a longitudinal profile different from the longitudinal profiles of the first, second and third elongate angled members, and a fourth one of said guide templates associated with said fourth one of said unbending channels and comprising a fourth one of said guide slots within said second one of said positioning blocks, said entry opening of said fourth one of said guide slots being disposed along said external surface of said second one of said positioning blocks and having a longitudinal profile that matches the longitudinal profile of the forward aspect of the fourth elongate angled member prior to straightening.

15. The straightening tool recited in claim 14 wherein said longitudinal profile of said entry opening of said first guide slot is matable in a complementary close fit with the longitudinal profile of the forward aspect of the first elongate angled member having an outer diameter of 4.0 mm and an initial bend of 12° along the forward aspect thereof, said longitudinal profile of said entry opening of said second one of said guide slots is matable in a complementary close fit with the longitudinal profile of the forward aspect of the second elongate angled member having an outer diameter of 4.5 mm and an initial bend of 45° along the forward aspect thereof, said longitudinal profile of said entry opening of said third one of said guide slots is matable in a complementary close fit with the longitudinal profile of the forward aspect of the third elongate angled member having an outer diameter of 4.0 mm and an initial bend of 40° along the forward aspect thereof, and said longitudinal profile of said entry opening of said fourth one of said guide slots is matable in a complementary close fit with the longitudinal profile of the forward aspect of the fourth elongate angled member having an outer diameter of 3.5 mm and an initial bend of 60° along the forward aspect thereof.

16. The straightening tool recited in claim 13 wherein said longitudinal profiles of said entry openings are matable with the longitudinal profiles of the first and second elongate angled members, respectively, with a complementary close fit.

17. A straightening tool for straightening an elongate angled member of an angled tissue cutting instrument in which the elongate angled member has a proximal length portion and an initial bend connecting the proximal length portion to a distal length portion extending from the bend to a distal end, comprising a positioning block attached to a handle;

an unbending channel in said positioning block configured to effect straightening of the elongate angled member, said unbending channel including a confinement passage for receiving the distal length portion of the elongate angled member and confining the distal length portion against movement radial to a central longitudinal axis of the distal length portion, said confinement passage being defined between a pair of planar internal walls of said positioning block in spaced parallel relation, said confinement passage comprising an abutment wall for abutment with the distal end of the elongate angled member within said confinement passage, said abutment wall extending perpendicularly between said internal walls, said unbending channel comprising an unbending slot in communication with said confinement passage for accommodating pivotal movement of the proximal length portion of the elongate angled member in a direction opposite the initial bend and relative to the distal length portion confined in said confinement passage; and a guide template corresponding to said unbending channel and comprising a guide slot disposed alone an external wall of said positioning block, said guide slot having a longitudinal profile along said external wall corresponding to the longitudinal profile of a forward aspect of the elongate angled member extending from the distal end to proximally of the bend, said guide slot comprising a first length section matching part of the proximal length portion extending from the bend, an angled length section matching the bend, and a second length section matching the distal length portion, said second length section being defined by said internal walls, said guide slot having a closed end defined by said abutment wall, said angled length section and said first length section being in communication with said unbending channel, wherein said unbending slot is bounded by a conforming surface that follows the longitudinal profile of said guide slot and by a contact surface extending at an angle to said confinement passage in a direction away from said conforming surface.

* * * * *